US011278218B2

United States Patent
Guy et al.

(10) Patent No.: US 11,278,218 B2
(45) Date of Patent: Mar. 22, 2022

(54) MULTIPLEXED TRANSDERMAL EXTRACTION AND DETECTION DEVICES FOR NON-INVASIVE MONITORING OF SUBSTANCES AND METHODS OF USE

(71) Applicant: THE UNIVERSITY OF BATH, Bath and North East Somerset (GB)

(72) Inventors: Richard Guy, Bath and North East Somerset (GB); Adelina Ilie, Bath and North East Somerset (GB); Luca Lipani, Bath and North East Somerset (GB); Floriant Doungmene, London (GB); Bertrand Gilbert Roger Jacques Dupont, Swarzedz (PL)

(73) Assignee: The University of Bath, Bath and North East Somerset (GR)

( * ) Notice: Subject to any disclaimer, the term of this patent is extended or adjusted under 35 U.S.C. 154(b) by 608 days.

(21) Appl. No.: 16/096,668

(22) PCT Filed: Apr. 26, 2017

(86) PCT No.: PCT/EP2017/059909
§ 371 (c)(1),
(2) Date: Oct. 25, 2018

(87) PCT Pub. No.: WO2017/186783
PCT Pub. Date: Nov. 2, 2017

(65) Prior Publication Data
US 2020/0008717 A1 Jan. 9, 2020

(30) Foreign Application Priority Data

Apr. 26, 2016 (GB) .................................. 1607265
Mar. 1, 2017 (GB) .................................. 1703300

(51) Int. Cl.
*A61B 5/00* (2006.01)
*A61B 5/145* (2006.01)
(Continued)

(52) U.S. Cl.
CPC ........ *A61B 5/14514* (2013.01); *A61B 5/1477* (2013.01); *A61B 5/1486* (2013.01);
(Continued)

(58) Field of Classification Search
CPC ............ A61B 5/14514; A61B 5/14532; A61B 5/1477; A61B 5/1486; A61B 2562/0215;
(Continued)

(56) References Cited

U.S. PATENT DOCUMENTS

| 5,279,543 A | 1/1994 | Glikfeld et al. |
| 5,362,307 A | 11/1994 | Guy et al. |

(Continued)

FOREIGN PATENT DOCUMENTS

| CA | 2450965 A1 | 3/2003 |
| CN | 101365381 A | 2/2009 |

(Continued)

OTHER PUBLICATIONS

Bae, et al., Roll-to-roll production of 30-inch graphene films for transparent electrodes, Nature Nanotechnology | vol. 5 | Aug. 2010, pp. 574-578.

(Continued)

*Primary Examiner* — May A Abouelela
(74) *Attorney, Agent, or Firm* — Stites & Harbison PLLC; Richard S. Myers, Jr.

(57) ABSTRACT

Multiplexed transdermal extraction and detection devices and systems for non-invasive monitoring of substances, such as glucose, are disclosed, as are methods of using these devices for substance monitoring in subjects.

31 Claims, 18 Drawing Sheets

(51) Int. Cl.
  *A61B 5/1477*    (2006.01)
  *A61B 5/1486*    (2006.01)
  *A61B 10/00*     (2006.01)
(52) U.S. Cl.
  CPC ...... *A61B 5/14532* (2013.01); *A61B 5/14546* (2013.01); *A61B 5/4845* (2013.01); *A61B 2010/008* (2013.01); *A61B 2010/0009* (2013.01); *A61B 2562/028* (2013.01); *A61B 2562/0215* (2017.08); *A61B 2562/125* (2013.01); *A61B 2562/164* (2013.01)
(58) Field of Classification Search
  CPC .............. A61B 5/14546; A61B 5/4845; A61B 2010/0009; A61B 2010/008; A61B 2562/028; A61B 2562/125; A61B 2562/164; A61B 2562/0209; A61B 2562/046
  USPC ...................................................... 600/347
  See application file for complete search history.

(56) References Cited

U.S. PATENT DOCUMENTS

| | | | |
|---|---|---|---|
| 5,730,714 | A | 3/1998 | Guy et al. |
| 5,911,223 | A | 6/1999 | Weaver et al. |
| 6,542,765 | B1 | 4/2003 | Guy et al. |
| 6,714,815 | B2 | 3/2004 | Guy et al. |
| 7,555,337 | B2 | 6/2009 | Guy et al. |
| 7,693,573 | B2 | 4/2010 | Guy et al. |
| 10,653,342 | B2* | 5/2020 | Rogers ............... A61B 5/6833 |
| 10,925,543 | B2* | 2/2021 | Rogers ............... A61L 31/028 |
| 2002/0019604 | A1 | 2/2002 | Tierney |
| 2005/0074810 | A1 | 4/2005 | Guy et al. |
| 2005/0096520 | A1 | 5/2005 | Maekawa et al. |
| 2009/0308742 | A1 | 12/2009 | Paranjape |
| 2012/0296186 | A1* | 11/2012 | Ouyang ............. A61B 5/14865 600/347 |
| 2013/0079605 | A1* | 3/2013 | Bandaru ............. A61B 5/1486 600/310 |
| 2013/0123595 | A1* | 5/2013 | Currie ............. A61B 5/150984 600/347 |
| 2015/0276206 | A1 | 10/2015 | Yamanaka et al. |
| 2017/0027514 | A1* | 2/2017 | Biederman .......... A61B 5/1451 |
| 2017/0224257 | A1* | 8/2017 | Rogers ............... A61B 5/0537 |
| 2017/0231571 | A1* | 8/2017 | Rogers ............... A61B 5/053 600/301 |
| 2017/0238851 | A1* | 8/2017 | Duhamel ........... A61B 5/14546 |
| 2017/0325724 | A1* | 11/2017 | Wang ................. A61B 5/14521 |
| 2018/0028099 | A1* | 2/2018 | Shekarriz ........... A61B 5/14546 |

FOREIGN PATENT DOCUMENTS

| | | |
|---|---|---|
| CN | 102119860 A | 7/2011 |
| EP | 0673622 A2 | 9/1995 |
| EP | 1077636 A1 | 2/2001 |
| EP | 1401532 B1 | 3/2004 |
| JP | 2004016489 A | 1/2004 |
| JP | 2010129385 A | 6/2010 |
| JP | 2013053925 A | 3/2013 |
| JP | 2015188475 A | 11/2015 |
| WO | WO96/00110 A1 | 1/1996 |

OTHER PUBLICATIONS

Bandodkar, et al., Tattoo-Based Noninvasive Glucose Monitoring: A Proof-of-Concept Study, Anal. Chem. 2015, 87, 394-398.

Bath, et al., Scanning Electrochemical Microscopy of Iontophoretic Transport in Hairless Mouse Skin. Analysis of the Relative Contributions of Diffusion, Migration, and Electroosmosis to Transport in Hair Follicles, Journal of Pharmaceutical Sciences, vol. 89, No. 12, 2000, pp. 1537-1549.

Chen, et al., Noncovalent Sidewall Functionalization of Single-Walled Carbon Nanotubes for Protein Immobilization, J. Am. Chem. Soc. 2001, 123, 3838-3839.

Cunningham, et al., In Vivo Glucose Sensing, Chemical Analysis a Series of Monographs on Analytical Chemistry and Its Applications, vol. 174, 2009, pp. 1-457.

Accuracy of the GlucoWatch G2 Biographer and the Continuous Glucose Monitoring System During Hypoglycemia : Experience of the Diabetes Research in Children Network . Diabetes Care, 27 (3): 722-726, 2004.

Gao, et al., Fully integrated wearable sensor arrays for multiplexed in situ perspiration analysis, Nature 2016, 529, 509-514.

Huang Y. et al., Nanoelectronic biosensors based on CVD grown graphene, 2010, Nanoscale, RSC, 2,1485-1488.

Kodali V. K. et al., Nonperturbative Chemical Modification of Graphene for Protein Micropatterning, 2011, Langmuir, 27, 863-865.

Kuila, T. Bose, S. Khanra, P. Mishra, A. K. Hoon Kim, N. Hee Lee, "Recent advances in graphene-based biosensor. Review.", Biosensors and Bioelectronics 26, 4637-4648 (2011).

Kwak Y. H. et al., 2012, Biosensors and bioelectronics, 37, 82-87.

Leboulanger et al., Reverse iontophoresis for non-invasive transdermal monitoring. Physiological Measurement, 25(3): p. R35, 2004.

Li, X., Zhu, Y., Cai, W., Borysiak, M., Han, B., Chen, D., Piner, R.D., Colombo, L. and Ruoff, R.S., Transfer of Large-Area Graphene Films for High-Performance Transparent Conductive Electrodes. Nano Letters, 2009, 9(12): 4359-4363.

Lipani, L., Dupont, B.G.R., Doungmene, F. et al. Non-invasive, transdermal, path-selective and specific glucose monitoring via a graphene-based platform. Nature Nanotech 13, 504-511 (2018).

Marro, D., et al., Contributions of electromigration and electroosmosis to iontophoretic drug delivery. Pharm Res, 2001. 18(12): p. 1701-1708.

Miao, C., Zheng, C. Liang, O. and Xie, Y.-H., Chemical Vapor Deposition of Graphene. In Physics and Applications of Graphene—Experiments, Mikhailov, S., Ed. InTech: 2011.

Polk, B.J., Stelzenmuller, A., Mijares, G., MacCrehan, W. and Gaitan, M., Ag/AgCl microelectrodes with improved stability for microfluidics. Sensors and Actuators B: Chemical, 2006, 114(1): 239-247.

Schmook, F.P., J.G. Meingassner, and A. Billich, Comparison of human skin or epidermis models with human and animal skin in in-vitro percutaneous absorption. International Journal of Pharmaceutics, 2001. 215(1-2): p. 51-56).

Sieg, A., R.H. Guy, and M.B. Delgado-Charro, Electroosmosis in Transdermal Iontophoresis: Implications for Noninvasive and Calibration-Free Glucose Monitoring. Biophysical Journal, 2004. 87(5): p. 3344-3350.

Tierney, et al., Electroanalysis of Glucose in Transcutaneously Extracted Samples. Electroanalysis, 12(9): 666-671, 2000.

Weaver et al . , Advanced Drug Delivery Reviews, 35:21-39, 1999.

Zoldák, G., et al., Irreversible Thermal Denaturation of Glucose Oxidase from Aspergillus niger Is the Transition to the Denatured State with Residual Structure. Journal of Biological Chemistry, 2004, 279(46): p. 47601-47609.

Guy, et al., The Glucose Pathfinder: Noninvasive, transdermal, path-selective and highly specific glucose monitoring on a graphene platform, MRC Confidence in concepts, 2015, pp. 1-12.

* cited by examiner

MULTIPLEXED TRANSDERMAL EXTRACTION AND DETECTION DEVICES FOR NON-INVASIVE MONITORING OF SUBSTANCES AND METHODS OF USE

CROSS REFERENCE TO RELATED APPLICATIONS

This application is a § 371 National State Application of PCT/EP2017/059909 filed Apr. 26, 2017 which claims priority to GB 1607265.4 filed Apr. 26, 2016 and GB 1703300.2 filed Mar. 1, 2017.

FIELD OF THE INVENTION

The present invention relates to multiplexed transdermal extraction and detection devices and systems for non-invasive monitoring of substances, such as glucose, and to methods of using these devices for substance monitoring in subjects.

BACKGROUND OF THE INVENTION

The GlucoWatch Biographer® remains the only non-invasive, glucose-monitoring device to have been approved for use in diabetic subjects by the US Food & Drug Administration (FDA). The technology uses iontophoresis (i.e., the application of a small direct current across two electrodes positioned on the skin surface) to induce the electro-osmotic extraction of a very small volume of interstitial fluid in which glucose is present at a concentration essentially identical to that in the blood (see U.S. Pat. Nos. 5,279,543, 5,362,307, 5,730,714, 5,911,223, 6,542,765, 6,714,815, 7,693,573 and 7,555,337). This tiny volume of fluid, of no more than a few microliters, is collected into and diluted within an aqueous, receiving gel (Leboulanger et al., *Reverse iontophoresis for non-invasive transdermal monitoring. Physiological Measurement,* 25(3): p. R35, 2004; Tierney, et al., *Electroanalysis of Glucose in Transcutaneously Extracted Samples. Electroanalysis,* 12(9): 666-671, 2000) and the glucose is then detected electrochemically via a glucose oxidase-mediated reaction. The area over which extraction is performed is about 3 cm$^2$ and the levels of glucose being measured in the collecting gel are on the order of micromolar (U.S. Publication No: 2002/019604). As a result, the GlucoWatch operates very close to its limit of detection, particularly when the diabetic subject is hypoglycaemic (*Accuracy of the GlucoWatch G2 Biographer and the Continuous Glucose Monitoring System During Hypoglycemia: Experience of the Diabetes Research in Children Network.* Diabetes Care, 27(3): 722-726, 2004). In addition, because the factor of dilution varies between subjects, and even within different skin sites on a single individual, it was essential to calibrate the device before each sampling period via a conventional 'finger-stick' measurement. For these, and other reasons, the GlucoWatch was not a commercial success and is no longer available. The provision of effective non-invasive glucose monitoring devices that avoid some of these drawbacks therefore remains an unresolved problem in the art.

SUMMARY OF THE INVENTION

Broadly, the present invention concerns devices, systems and methods for transdermal extraction and detection of substances, such as glucose via reverse iontophoresis, that enable the non-invasive monitoring of their levels in subjects. The devices, systems and methods of the present invention preferably allow the semi-continuous or continuous monitoring of their levels in subjects. The devices, systems and methods operate through transdermal extraction of the substances via preferential pathways in the skin, typically through skin appendages such as skin pores, hair follicles and sweat glands. The present invention differs from prior art approaches for the transdermal extraction and detection monitoring of substances in its ability to access and sample the preferential pathways individually via a multiplexed array of sensor pixels, each sensor pixel performing the dual roles of substance (e.g., glucose) extraction and detection. This may be compared to the prior art sampling approaches which employ a comparatively large skin area and which have the inevitable result of combining samples of the substance which are transdermally extracted via different extraction mechanisms and over a plurality of skin structures. The ability of the present invention to interrogate single preferential pathways with a single sensor pixel in an array has the advantage that it enables clinically relevant transdermal monitoring to be implemented, typically without the need for finger-stick (or an equivalent method of) calibration. The present invention achieves these aims through the use of a miniaturised iontophoretic sampling device designed with an array of sensor pixels dimensioned so that one or more of the sensor pixels samples analyte extracted via a preferential pathway.

Although the devices, systems and methods of the present invention are particularly useful for the non-invasive monitoring of glucose, the present invention may also be employed for the detection of other transdermally extractable substances (analytes), such as diagnostic markers, drugs, substances of abuse and toxins. Specific examples of transdermally extractable analytes include glucose; markers of oxidative stress such as glutathione, reactive oxygen and nitrogen species or peroxynitrites; metal ions such as Na$^+$ and K$^+$; markers of kidney disease, such as urea or iohexol in paediatric patients; markers of skin health, including the constituents of so-called 'natural moisturizing factor' (NMF), which is intimately involved in skin barrier function and skin hydration; drugs including therapeutic drugs, e.g. for continuous monitoring, lithium, chemotherapeutic agents such as fluorouracil and methotrexate, theophylline for asthma treatment, antidepressants such as amitriptyline HCl; hormones such as insulin, prostaglandin or steroids, and other analytes such as lactate, alcohol, sucrose, galactose, uric acid, alpha amylase, choline and L-lysine, acetylcholine, pilocarpine (e.g. for cystic fibrosis diagnosis). A preferred list of substances includes glucose, lithium, lactate, ammonium, urea, uric acid, potassium, ethanol, valproate, glutathione, phenylalanine, amino acids, constituents of the skin's natural moisturizing factor (NMF), iohexol, therapeutic monitoring of various compounds representing anti-depressive and anti-cancer drugs, prostaglandins, steroids and other drug classes and drugs that will be evident to those skilled in the art. An extensive list of substances that may be monitored using non-invasive sampling techniques of the present invention is provided in U.S. Pat. No. 5,279,543 which is expressly incorporated by reference in its entirety, see especially Table 4.

In one particular application, the devices, systems and methods of the present invention may be used for monitoring markers of oxidative stress, for example for the non-invasive monitoring and indirect detection of the highly-damaging reactive oxygen and nitrogen species arising from environmental stressors such as ultraviolet radiation (UV) and pollution. Molecules such as glutathione or stabilised derivatives of peroxynitrite may be extracted and electrochemically detected. Glutathione is present in physiological conditions in two forms: as GSH, the reduced form, and GSSG, the oxidised form. When reactive oxygen species are produced in a concentration that could cause cell damage, GSH is oxidised to GSSG. The ratio of GSH/GSSG in tissue is therefore highly correlated with oxidative stress. Peroxynitrite is produced in vivo by the reaction of superoxide with nitric oxide and contributes to cell damage during oxidative stress. The capacity to detect and monitor these molecules non-invasively would be a major advance in the detection of and development of protection strategies against oxidative and/or nitrosative stress.

Accordingly, in a first aspect, the present invention provides a multiplexed, transdermal extraction and detection device for non-invasive monitoring of one or more substances in a subject, the device comprising an array of sensor pixels, each sensor pixel comprising:
  (a) a substrate comprising a set of electrodes for applying a current to the subject's skin for transdermally extracting the one or more substances from the interstitial fluid by electro-migration and/or by electro-osmosis;
  (b) a reservoir associated with the sensor pixel, the reservoir containing a volume of gel for receiving the transdermally extracted substances from the sensor pixel;
  (c) a set of detection electrodes for electrochemical detection of the concentration of the one or more transdermally extracted substances present in the reservoir associated with the sensor pixel;
  wherein the array of sensor pixels is configured so that at least one of the sensor pixels is capable of extracting the one or more substances via a preferential pathway on the subject's skin.

In a further aspect, the present invention provides the use of a multiplexed, transdermal extraction and detection device of the present invention for non-invasive monitoring of one or more substances in a subject.

In a further aspect, the present invention provides a multiplexed, transdermal extraction and detection system for non-invasive monitoring of one or more substances in a subject, the system comprising:
  (i) a device comprising an array of sensor pixels, each sensor pixel comprising:
    (a) a substrate comprising a set of electrodes for applying a current to the subject's skin for transdermally extracting the one or more substances from the interstitial fluid by electro-migration and/or by electro-osmosis;
    (b) a reservoir associated with the sensor pixel, the reservoir containing a volume of gel for receiving the transdermally extracted substances from the sensor pixel; and
    (c) a set of detection electrodes for electrochemical detection of the concentration of the one or more transdermally extracted substances present in the reservoir associated with the sensor pixel;
    wherein the array of sensor pixels is configured so that at least one of the sensor pixels is capable of extracting the one or more substances via a preferential pathway on the subject's skin; and
  (ii) a data acquisition, control and processing system comprising:
    (a) an acquisition and control system controlling access to each of the individual pixels of the array, and for each of them the extraction/detection functions;
    (b) a data processing system capable of distinguishing a sample of a transdermally extracted substance obtained by the device via a preferential pathway from that extracted via other pathways, so that samples of the transdermally extracted substance via the preferential pathway are used for estimating the concentration of the one or more substances in the subject.

In a further aspect, the present invention provides a method for non-invasive monitoring of one or more substances in a subject, wherein the method employs a multiplexed, transdermal extraction and detection system comprising:
  (i) a device in the form of an array of sensor pixels, each sensor pixel comprising:
    (a) a substrate comprising a set of electrodes for applying a current to the subject's skin for transdermally extracting the one or more substances from the interstitial fluid by electro-migration and/or by electro-osmosis;
    (b) a reservoir associated with the sensor pixel, the reservoir containing a volume of gel for receiving the transdermally extracted substances from the sensor pixel;
    (c) a set of detection electrodes for electrochemical detection of the concentration of the one or more transdermally extracted substances present in the reservoir associated with the sensor pixel;
    wherein the array of sensor pixels is configured so that at least one of the sensor pixels is capable of extracting the one or more substances via a preferential pathway on the subject's skin;
  and
  (ii) a data acquisition/processing system capable of controlling extraction/detection within each of the pixels of the array device, and distinguishing a sample of a transdermally extracted substance obtained via a preferential pathway from that extracted via other pathways, so that samples of the transdermally extracted substance via the preferential pathway are used for estimating the concentration of the one or more substances in the subject;
  the method comprising
  (i) contacting the array of sensor pixels with the skin of the subject;
  (ii) using the extraction electrodes to apply a current to the skin of the subject to transdermally extract one or more substances from the interstitial fluid by electro-migration and/or by electro-osmosis at the sensor pixels in the array;
  (iii) absorbing the fluid samples into the gel reservoirs of the sensor pixels in the array;
  (iv) electrochemically detecting the one or more substances absorbed into the gel reservoirs;
  (v) analysing the concentrations of the one or more substances present in the individual gel reservoirs to determine which sensor pixels extracted samples via a preferential pathway in the skin of the subject;
  (vi) using the substance concentrations from the samples extracted via preferential pathways to determine the concentration of the one or more substance in the body of the subject.

In all aspects and embodiments of the present invention, a preferred substance that can be monitored is glucose, in particular non-invasive and preferably semi-continuous or continuous glucose monitoring in the management of diabetes.

Preferably, the extraction and detection electrodes at each sensor pixel are laid down on a flexible, and optionally transparent, substrate. Conveniently, the flexible substrate may be formed from a polymer, such as polyethylene terephthalate (PET). In one preferred embodiment, the set of extraction electrodes comprises two electrodes, for example a Ag and AgCl electrode pair. Generally, the set of detection electrodes comprises two or three electrodes for example a set of electrodes comprising AgCl and graphene electrodes, and optionally a Pt electrode. The use of graphene as an electrode material has the advantage that it can be readily patterned into sensor pixels of a suitable size (e.g. about 2×2 $mm^2$) via techniques such as plasma etching using standard optical lithography or directly by shadow-masking, made by controlled vapour deposition. Alternatively, a graphene-based nanoflake ink can be printed using printing technologies. Advantageously, graphene can be used also to form electrical interconnects to the sensor pixels. In all embodiments, platinum nanoparticles (Pt NPs) are immobilised on the graphene or, alternatively, incorporated within the printed graphene, forming part of the set of detection electrodes to produce a catalytic effect that is capable of boosting the level of measurable current against the background noise for analyte (e.g., glucose) detection and decrease the overpotential needed to perform the electrochemical reaction. The platinum nanoparticles may be immobilised on the sensor pixels by techniques such as electrochemical deposition or formed by sputtering. These platinum nanoparticles are immobilised on the graphene electrode to amplify, for example, the signal from the hydrogen peroxide produced from the enzymatic reaction of glucose in the extracted samples and glucose oxidase.

Using such approaches, sets of electrodes for both substance extraction and electrochemical detection are then provided at each sensor pixel in a way that means that the sensor pixels are individually addressable so that the device is capable of distinguishing a sample of a transdermally extracted substance obtained via a preferential pathway measured at one or more sensor pixels from that extracted via other pathways that is measured at other sensor pixels.

In addition to the substrate supporting the extraction and detection electrodes, the device may comprise a patterned supporting membrane, generally in the form of a flexible membrane formed from an elastomer, such as polydimethylsiloxane (PDMS). In the device, the supporting membrane is overlaid on top of the substrate. Conveniently, the supporting membrane has a pattern of holes formed to match the pattern of the sensor pixels, and provides definition and mechanical support for an array of gel reservoirs that fill the pattern of holes. This gel reservoir-containing membrane provides the interface between the device and the skin of the user. The gel reservoirs fill the holes of the membrane so that they are in contact with the substrate. For optimum function, preferably the gel is also flush with the outer surface of the membrane so that it is capable of coming into contact with the skin for receiving the one or more substances extracted by the extraction electrodes. Preferably the thickness of the supporting elastomer membrane is less than 0.5 mm, more preferably less than 0.4 mm, more preferably less than 0.3 mm, more preferably less than 0.2 mm, and most preferably on the order of 0.1 mm. A range of preferred thickness of gel forming the sensor pixels is between 0.05 mm and 0.2 mm. In a preferred embodiment, the elastomer membrane with the encased hydrogel is then positioned on top of the array of sensor pixels so that the gel pixels align with the sensor pixels. By way of example, the volume of gel in a sensor pixel is generally less than about 30 μL, more preferably less than about 20 μL, and still more preferably less than 10 μL. In one preferred configuration, volume of gel in a sensor pixel is generally between 0.1 μL and 30 μL, more preferably between 0.1 μL and 10 μL, and still more preferably between for example 0.2 μL and 2 μL. Conveniently, the gel is a hydrogel, such as agarose.

In one preferred arrangement, the reservoirs comprise an enzyme-containing gel for detecting substances extracted using the device. For the detection of glucose, the enzyme glucose oxidase is entrapped in the hydrogel reservoirs to provide the sensor pixels with specificity of response to glucose by reacting with glucose in the sample to produce hydrogen peroxide for detection by the detection electrodes. In this way, the sensor will not respond to interfering species that can be present in the iontophoretically extracted fluid. Typically, the enzyme is mixed with the hydrogel while in the liquefied state. When the supporting membrane is fabricated, enzyme and liquefied hydrogel are injected (sequentially, or in a single step, using a mixture of the two, depending on the thermal characteristics of both enzyme and hydrogel) using a micro-dispenser into each of the holes of the supporting membrane and allowed to solidify. The hydrogel is allowed to set to a semi-solid state, which typically corresponds to the set volume being about ⅔ of the initial volume. This state of the hydrogel facilitates both glucose diffusion through the gel and effective electron transfer during electrochemical sensing. In one embodiment, the supporting membrane and gel reservoirs are designed to be a replaceable part that mates with the electrode substrate, thereby enabling the electrodes to be reused.

The device of the present invention can also be made using screen printing technologies to produce a defined array of sensor pixels and the means for interconnecting them to the outside world. In these embodiments the sets of electrodes and their interconnects are printed onto the flexible substrate, for example using a graphene flake-based ink, a Ag-based ink and a Ag/AgCl-based ink, respectively.

In all approaches, miniaturisation enables the spacing between the electrodes in a sensor pixel to be chosen so that the working and counter electrodes are close enough to the reference and iontophoresis electrodes in order to minimise the ohmic potential drop in solution, as well as to allow the extracted substances (e.g., glucose) to reach rapidly and efficiently the detection electrodes.

Generally, the devices of the present invention include an array of sensor pixels that has sufficient pixels to ensure that at least one sample of the substance is extracted via a preferential pathway, and more preferably so that a plurality of samples are so extracted. This may be achieved using an array of sensor pixels that comprises at least 16 sensor pixels, and more preferably an array of sensor pixels that comprises at least 64 sensor pixels. In some cases, advantageously the array of sensor pixels comprises between 10 and 100 sensor pixels, for example the array of sensor pixels comprises 16 or 64 sensor pixels. Preferably, the sensor pixels have an area between 1.0 $mm^2$ and 100.0 $mm^2$, for example an area between 2.0 $mm^2$ and 50.0 $mm^2$ or an area between 3.0 $mm^2$ and 10.0 $mm^2$.

The acquisition, control and processing of the data of the device array may be implemented via bespoke software using a System on Chip (SoC). The devices, systems and methods of the present invention can output the results of monitoring the one or more substances wirelessly to any convenient output device known in the art, such as a personal "smart" device (e.g. smart phone, wrist-band or smart watch), tablet or other computer. This will result in the display of the results, or allow more sophisticated scenarios, such as the setting of alarms warning of low-blood sugar.

Embodiments of the present invention will now be described by way of example and not limitation, with reference to the accompanying figures. However various further aspects and embodiments of the present invention will be apparent to those skilled in the art in view of the present disclosure.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Non-Invasive Substance/Analyte Monitoring

Figure 1:
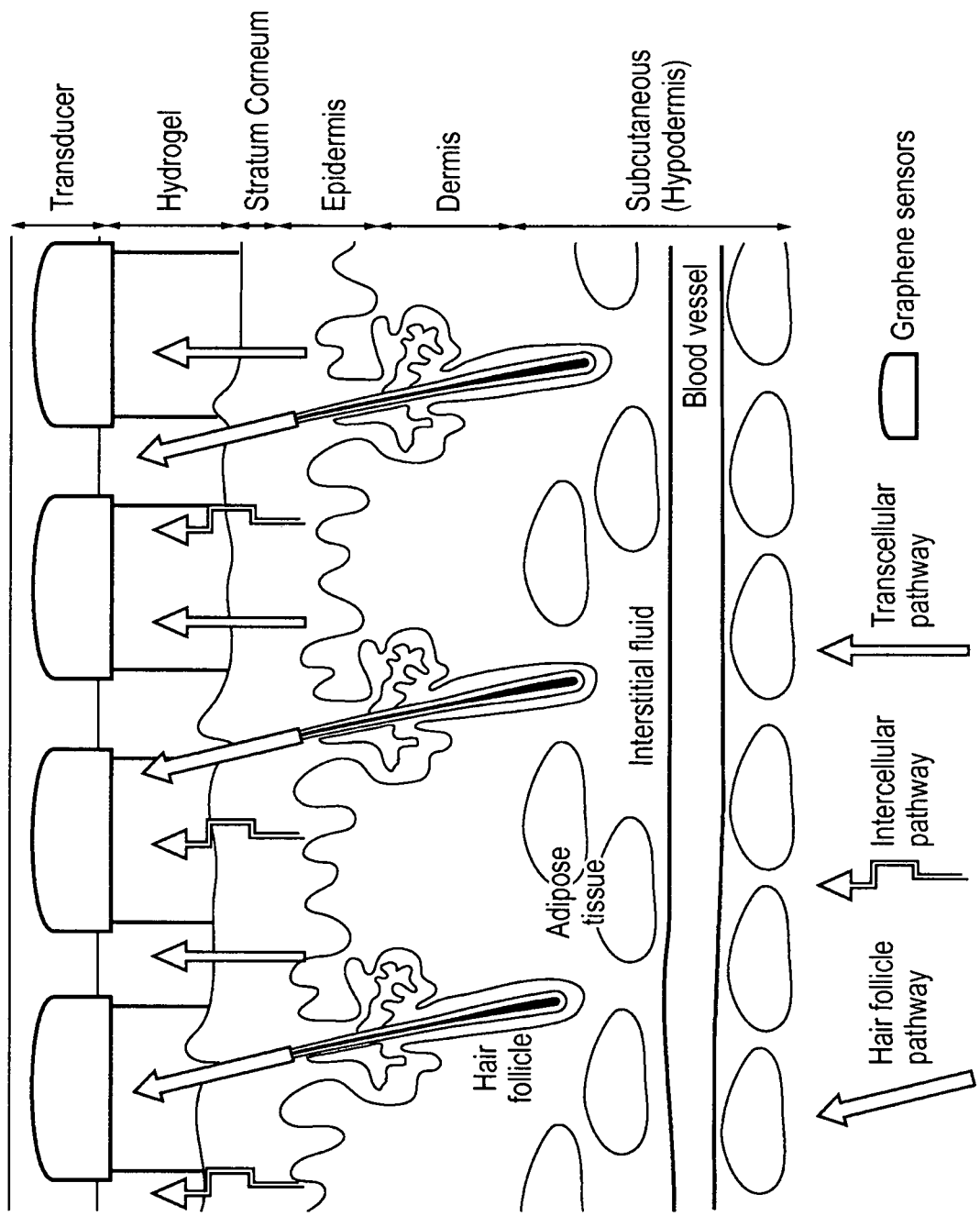
FIG. 1. "Glucose Pathfinder" principle. Preferential glucose pathways (hair follicles) are targeted by individual, miniature pixel detectors. With a sufficiently dense pixel array, a number of such pathways will be sampled randomly by the pixelized sensors. The concentration of glucose extracted via the hair follicles is in a fixed relationship to that in the interstitial fluid.
Figure 2:
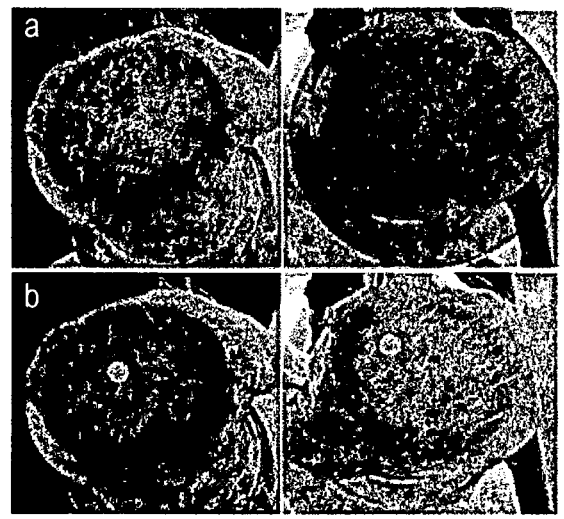
FIG. 2. Comparison between "GlucoWatch" and "Glucose Pathfinder" in respect to glucose sampling through skin of varying hair density (low density, left-side; high density, right-side): (a) the large area sampling of the "GlucoWatch" leads to variable dilution factors; (b) single pixel device in the "Pathfinder" array has a sufficiently small area to enable the sampling of only one follicular pathway—this guarantees a fixed dilution factor for the extracted glucose irrespective of the hair density.

While the following discussion focuses on the specific case of glucose monitoring, it will be clear to those skilled in the art that other substances/analytes may be extracted non-invasively through the skin through electro-migration and/or electro-osmosis, which accompanies the process of reverse iontophoresis that is established when an electric field is applied across skin. In the case of glucose, which is a polar and water-soluble substance, but carries no net charge under physiological conditions, its mechanism of iontophoretic extraction is only via electro-osmosis. This process occurs primarily via low resistance, preferential pathways associated with skin appendages such as skin pores, hair follicles and sweat glands (e.g., see FIG. 1 of Weaver et al., Advanced Drug Delivery Reviews, 35:21-39, 1999). These appendages penetrate subcutaneously down to the interstitial fluid which bathes the cells and which contains the substances of interest, such as glucose (FIG. 1). This extraction principle has been utilized in a previous transdermal technology, the "GlucoWatch® Biographer". In that case, glucose is extracted indiscriminately across a comparatively large area, of about 3.5 cm$^2$, into a single large volume gel reservoir where the sampled glucose was then measured. Importantly, this prior art approach did not recognise or exploit the advantages offered by single pathway sampling and instead the large area of extraction led to variable dilution factors as the hair density varies between skin regions and from user to user (FIG. 2a). One consequence of this is that periodic (and at least daily) calibration of the GlucoWatch® Biographer through "finger-stick" blood sampling was required.

In contrast, the devices, systems and methods of the present invention employ a single pathway sampling concept that circumvents the need for finger-stick calibration, as the dilution factor of the extracted substance(s) is fixed by the geometric characteristics of the miniaturised single pixel device of an array of sensor pixels (FIG. 2b), so that the density of the skin appendages, such as skin hair follicles, through which substances are extracted has no influence on the determination of substance concentration in the transdermally extracted fluid. In one preferred implementation of the present invention for glucose monitoring, this capability, based upon specific technical achievements of device size/ glucose operation range and sensitivity/material implementation, is a unique aspect of our technology. Transdermal glucose monitoring hence becomes truly non-invasive, promising to satisfy an important unmet medical need.

In addition, the devices, systems and methods of the present invention can use a data acquisition and processing system (e.g., via software-control implemented, for example, using System on Chip technology) allowing analysis of the data acquired by each sensor pixel in the multiplexed array, identifying the sensor pixels that are sampling the preferential glucose pathways, and retaining and processing the data produced from these sensor pixels, as distinct from other sensor pixels in the array that either do not produce a useful signal or else produce a signal that arises from samples extracted via other pathways or mechanisms. In this way, data that does not reflect the glucose levels in the interstitial fluid can be discarded. A further advantage of the approach used on the present invention is that it enables the identification of the sensor pixels producing meaningful data in the early stages of an acquisition/read-out cycle, allowing one to reduce the overall processing time for the determination of the level of the one or more substances.

The array contains an optimised number (see below) of miniaturised, graphene sensor pixels. Each pixel (FIG. 3) performs the critical functions of glucose extraction and detection, and comprises (a) an individual enzyme-bearing gel reservoir, into which glucose is extracted transdermally, (b) an extraction circuit that allows the glucose to be extracted into the gel reservoir, and (c) an electrochemical, enzyme-based glucose detector based on a platinum nanoparticle (NP)-decorated graphene material. In its final form, the array is integrated into a flexible patch with, potentially, a disposable element (see below), and, ultimately, has a wireless readout.

1. Geometry Considerations

To optimise the functionality of the array, the number of its pixels and their geometrical dimensions need to be carefully selected, according to the following criteria.

Figure 4:
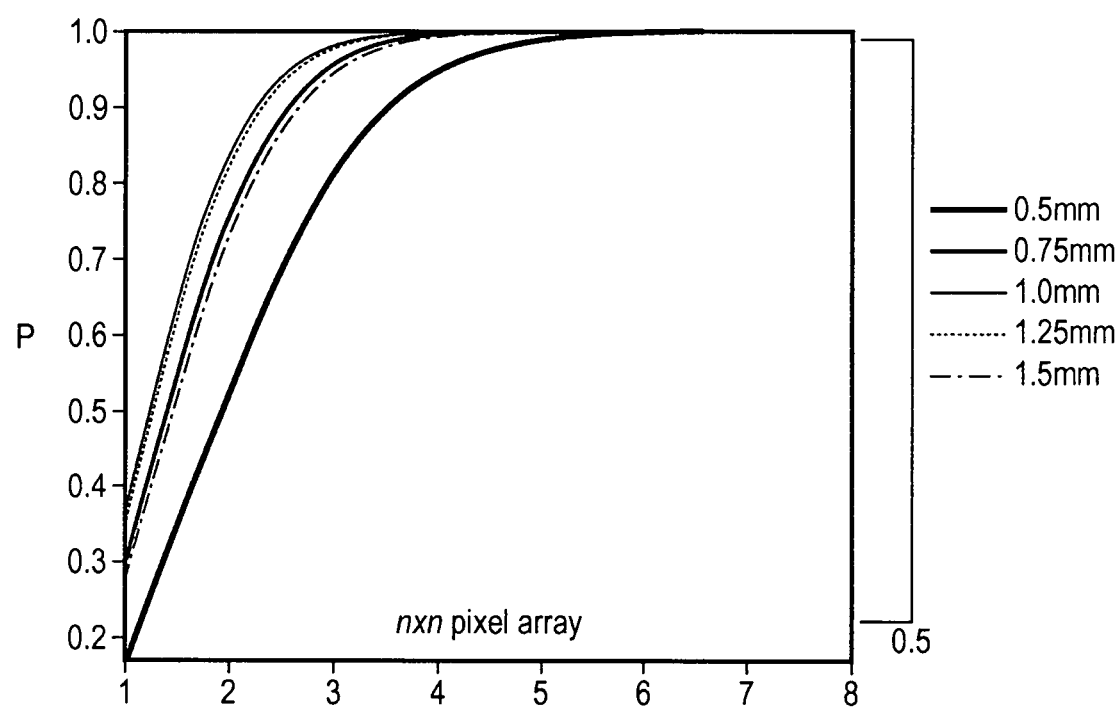
FIG. 4. (a) Probability P that the device has at least one working pixel with a single pathway per pixel, as a function of pixel radius and for various numbers of pixels in the array. (b) Probability P that the device has at least one working pixel with a single pathway per pixel, as a function of the number of pixels in the array and for various pixel radii.

Criterion 1:

The number of pixels in the array and their number per unit area is dictated by the probability P of at least one hair follicle "hit" using the chosen geometry, and that no more than one hair follicle is probed by an individual pixel. As input parameters for such estimations, the overall area of the device patch was set to 2×2 cm$^2$ (for practical reasons), and a human hair distribution centred about a peak value of 24 follicles per cm$^2$ (which is encompassed by the average hair distribution of 18 to 32 follicles per cm$^2$ on the human forearm) FIG. 4(a) shows that a 4×4 pixel array of 2 to 3 mm diameter cylinders of enzyme-containing gels guarantees at least one follicular "hit". Outside this optimum range, P becomes less than 1 for (i) small radii, when the total active area of the monitor is too low, and (ii) large radii, when a pixel can hit more than one preferential pathway. FIG. 4(b) shows this non-monotonic behaviour as a function of pixel radius more clearly. Both graphs (a) and (b) show that, by increasing the number of pixels in the array, more than one pixel per array will hit a preferential pathway, thus ensuring useful redundancy.

In a full-scale implementation, an 8×8 array provides useful redundancy for probing the privileged glucose pathways.

Accordingly, the multiplexed iontophoretic sampling devices of the present invention preferably comprise an array spanning about 2×2 cm$^2$, and comprising between 4 and 100 sensor pixels, and more preferably between 10 and 80 sensor pixels. In some embodiments, the array of sensor pixels comprises 4, 9, 16, 25, 36, 49 or 64 sensor pixels, for example in arrays 2×2, 3×3, 4×4, 5×5, 6×6, 7×7 or 8×8 sensor pixels. While in some embodiments, the sensor pixels are disposed in a square array, other arrangements of sensor pixels may be used.

Criterion 2:

If the diameter/area of the enzyme-encasing gel within a pixel is as estimated above, its volume is determined by the requirement that the glucose concentration range achieved in the pixel reservoir falls well within the full available range of the sensor. Taking the hypoglycaemic and hyperglycaemic blood concentrations to be 3.5 and 12 mM, respectively, 11 µM and 36 µM are obtained after their dilution in 24 µl of gel. These values were obtained for an extraction current of 0.2 mA over 1-hour extraction period, and are consistent with the value of glucose extraction flux through a single follicular pathway of 3.5 nmol·mA$^{-1}$·hr$^{-1}$ at 10 mM subdermal glucose concentration, as determined in section 3 ("Proof-of-principle"), below. FIG. 6 shows the range of diluted concentrations obtained with these selected geometries mapped (in red) onto the full glucose concentration range to which a typical, individual pixel sensor responds: (a) experiment using external (wire type) Pt and Ag/AgCl electrodes; (b) experiment using on-chip integrated electrodes.

The volume of the gel reservoir and the extraction conditions set the value of the fixed conversion factor between the interstitial fluid glucose concentration and the one that is achieved in the pixels of the array. By decreasing the reservoir volume, the concentration increases, allowing for the extraction time and iontophoretic current to be decreased while still obtaining a similar working concentration range to the one in FIG. 6. For example, a reduction in the volume of the gel reservoir by a factor of ~60 allows the hypo- to hyper-glycaemic blood glucose concentration range to be mapped onto the 10 to 40 µM glucose concentration within the gel reservoir, to be achieved using extraction current and period of 0.02 mA and 10 minutes, respectively (a follicular glucose flux value of 3.5 nmol·mA$^{-1}$·hr$^{-1}$ at 10 mM subdermal glucose concentration was used for this estimation).

Criterion 3:

The gel dimensions also have an impact on the overall duration of the glucose extraction/read-out cycle. The thickness of the gel has to be minimised to decrease the time needed for the extracted glucose to diffuse across the gel, from the side facing the skin to the side facing the graphene sensor. Targeted thickness range is on the order of 0.1 mm (Tierney, et al., *Electroanalysis of Glucose in Transcutaneously Extracted Samples*. Electroanalysis, 12(9): 666-671, 2000), which is thereby the most preferred thickness value of the gel reservoir.

To summarise, for example, a volume of gel reservoir of 2 mm diameter and 0.1 mm thickness would allow the extraction current and period to be decreased, for example, to 0.02 mA and 10 minutes, respectively, while achieving the same glucose concentration range, of 10 to 40 µM, in the gel reservoir, as mapped in red on FIG. 6.

In all designs, for a given pixel device within the array, the active areas of extraction and detection electrodes fit within the pixel area. An example of typical dimensions within a pixel area is given in FIG. 5: the unit cell of the array (pixel area) was chosen to be 5×5 mm$^2$, with the active regions of the electrodes occupying a 4×4 mm$^2$ area, and the footprint area of the gel reservoir within which glucose is extracted (delineated with a dotted line in FIG. 5) occupying a disk region of 3 mm in diameter. In arrays with a larger number of pixels, all electrode dimensions and spacing will be decreased appropriately to fit within smaller unit cells, maintaining the lowest value for the gel reservoir diameter around 2 mm diameter (in agreement with the single follicular pathway "hit probability" calculations from FIG. 4). In a final form, the whole patch-like monitor, including surrounding area for the interconnects and System on Chip, will fit most likely within a 3×3 to 4×4 cm$^2$ area, depending on the degree of miniaturization used.

2. Choice of Materials and Device Realization Strategies

The main materials used to construct the glucose monitor in this embodiment are: (i) a graphene film decorated with platinum nanoparticles, together forming the sensing material, (ii) an enzyme, glucose oxidase, which in an electrochemical reaction with glucose produces hydrogen peroxide, the reaction product detected by the electrochemical graphene sensor, (iii) a hydrogel (based on a polymers such as agarose, chitosan, ethyl cellulose, or methyl cellulose) used to encase the enzyme, and (iv) a bio-compatible elastomer (e.g. silicone rubbers, such as polydimethylsiloxane (PDMS) or PlatSil 7315, yielding thicknesses in the hundred micron range; or parylene, for designs where thicknesses below 100 μm are sought) for creating a perforated membrane, used to provide mechanical support and definition for the gel reservoirs of each pixel. Graphene is the material of choice for flexible electronics. Here it was chosen due to its mechanical resilience to bending and flexing, its ease towards patterning and device integration through standard microfabrication techniques (characteristics that are necessary to create the pixelized array), its compatibility with green electronics, and not least of all its potential to reduce the cost in a commercial product compared with noble metal electrochemical electrodes. In combination with Pt nanoparticles (or other catalytic particles), the electrochemical response towards glucose of the graphene/Pt NPs electrode spans many orders of magnitude and its sensitivity is excellent (see section 3). Finally, in a preferred embodiment, graphene can be used not only to provide the active area of the electrochemical pixel sensors, but also the electrical interconnects that link these sensing regions to the outside world (FIG. 5). Depending on the realization strategies (see below), the types of graphene to be used can be either atomically thin layers produced by CVD, or a graphene nano-flake ink used to create the printed regions.

The realization of the pixel array is not restricted to the sensing materials mentioned above. Other sensing materials could be used, such graphene/Pt NPs (or other catalytic particles) further functionalized with Prussian Blue (or an equivalent, with the role to further decrease the working potential), carbon-based electrodes (including carbon nanotubes), Prussian Blue (or an equivalent) alone, metal electrodes traditionally used in electrochemistry, or a combination of them.

To build the pixel array, several realization strategies can be employed:

Strategy No. 1

1. A patch of, typically, 1.6×1.6 cm$^2$ of large area graphene produced by Chemical Vapour Deposition (CVD) is transferred onto a flexible (potentially, also transparent) substrate, using either a wet or dry process. The substrate can be polyethylene terephthalate (PET), which is the substrate of choice for a variety of flexible electronics applications, including those based on graphene. Other examples of possible flexible substrates are polyethylene naphtalate (PEN), or polyimide films (such as kapton.

2. Graphene is then patterned into pixels of about 2×2 mm$^2$ via plasma etching using standard optical lithography or, directly, by shadow-masking; in this way, unwanted graphene regions are etched away. This permits the definition of both the pixel sensing areas and, additionally (though not essentially), the electrical interconnects to the outside world based on graphene, as in FIG. 5.

3. Pt nanoparticles are then immobilised onto graphene pixel sensing areas (see section 4, "Supporting Methods") by electrochemical deposition; or, alternatively, can be formed by sputtering. Their catalytic effect boosts the level of measurable current against the background noise for glucose detection, and decreases the overpotential needed to perform the reaction.

Figure 3:
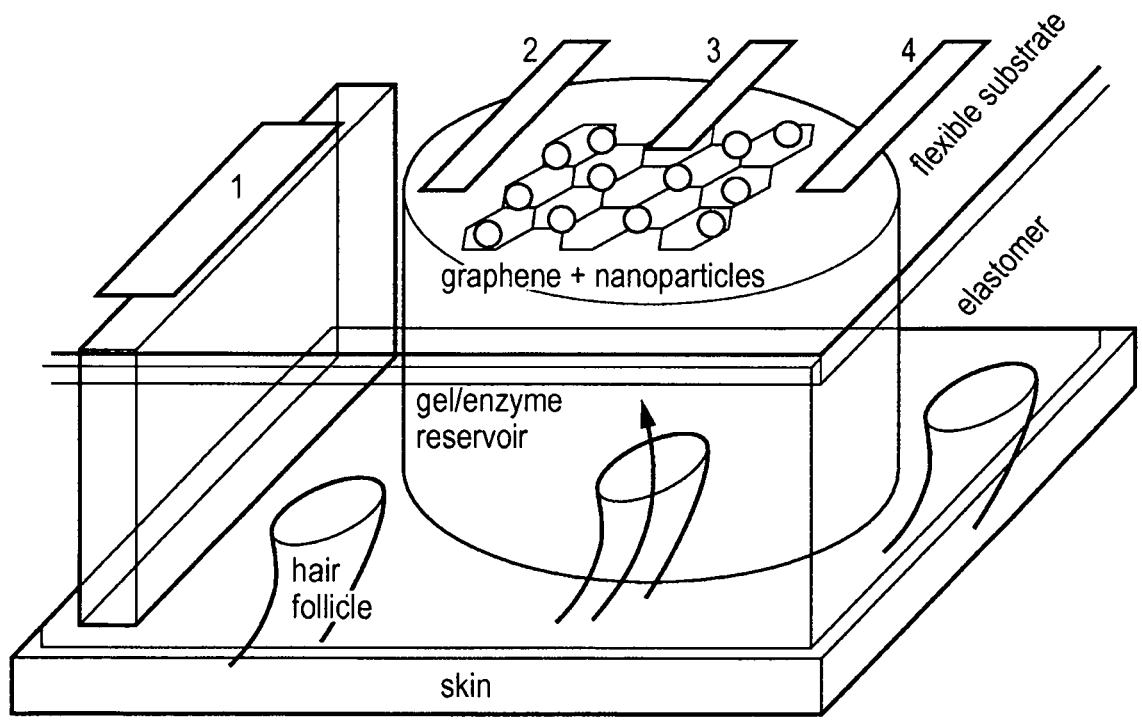
FIG. 3. Schematic of an individual extraction and detection miniature pixel: electrodes 1 (Ag) & 2 (Ag/AgCl) perform glucose extraction; electrodes 2 (Ag/AgCl, reference electrode), 3 (graphene decorated with Pt nanoparticles, graphene/Pt NPs, the working electrode), and 4 (Pt, counter electrode) detect glucose electrochemically. The catalytic Pt nanoparticles on graphene boost the detection signal. The electrodes 2, 3 and 4 are sized so that they fit appropriately under a miniaturized enzyme-encasing gel reservoir, into which glucose is extracted. The gel reservoir is formed inside the holes of a supporting elastomer membrane. Preferred sizes are given below.

4. Electrodes for both glucose extraction and electrochemical glucose detection are then created within each pixel. FIG. 3 shows an early design, where electrodes 1 and 2, made of Ag and AgCl, respectively, are used for extraction; while electrodes 2, 3 and 4, made of AgCl, graphene, and Pt, respectively, are used for detection. In more recent designs, FIG. 5, the Pt electrode has been removed.

These electrodes of different materials (Ag, AgCl, Pt) are defined conveniently by several stages of thermal evaporation or sputtering through custom-made stencil masks, or alternatively, they could also be realized using standard lithography. AgCl regions can be formed beginning from an underlying Ag layer which is then chemically converted (e.g., by reaction with $FeCl_3$) into AgCl, or by electrochemical anodization of a pre-deposited Ag layer (see section 4, "Supporting methods").

5. A patterned insulating layer (such as an oxide or an insulating polymer) is deposited onto the array device. This step will leave exposed only the active areas (where glucose extraction and detection takes place) of each pixel, covering everything else, i.e., all the electrical interconnects linking the active area of each pixel device within the array to the connectors of the acquisition and control System on Chip. In this way, interconnects are protected against humidity, liquids and sweat during operation.

6. A thin, flexible and free-standing membrane of elastomer (such as PDMS, Platsil or Parylene) or similar material (see schematics in FIG. 3), with holes in a pattern matching the graphene pixel array pattern is formed separately. The membrane may be formed by methods such as spin-casting, polymer vapour deposition, or injection moulding. This membrane provides definition and mechanical support for the enzyme-containing gel reservoirs which subsequently fill the holes in the membrane and are flush with the membrane surface. Preferred thickness of this membrane is on the order of 0.1 mm, a requirement imposed by the preferred thickness of the gel reservoir; such a thickness can be obtained, for example, by spin-casting. The elastomer-gel unit also provides the interface between the device and the skin. In a preferred embodiment, the elastomer membrane with the encased gel is then positioned on top of the graphene pixel array so that the gel pixels align with the graphene sensing pixels.

7. The enzyme glucose oxidase is entrapped in the hydrogel reservoir (see section 4, "Supporting Methods") to provide specificity (to glucose) to the sensor's response. In this way, the sensor will not respond to interfering species that can be present in the iontophoretic extract. The enzyme is mixed with the hydrogel while in liquefied state.

8. Depending on their thermal characteristics, the enzyme and liquefied hydrogel are injected sequentially (to avoid enzyme denaturation), or mixed together, using a microdispenser, into each of the holes of the supporting membrane, and allowed to solidify. In the case of full-size arrays, commercial micro-dispensing systems such as Biodot xyz or Biojet may be used. Other methods for the realization of this step may involve some form of patterning or mechanical transfer.

The hydrogel is allowed to become semi-solid, at which point its volume is about ⅔ of the initial value; the semi-solid nature of the hydrogel facilitates both glucose diffusion through the gel and effective electron transfer during electrochemical sensing. The elastomer unit with the encased gel may represent the replaceable part of the device.

Strategy No. 2

This strategy makes extensive use of screen printing technologies for the definition of the array's pixels and interconnects that link them to the outside world. In a preferred realization (refer to FIG. 5), various regions of the array are created as follows: (i) the electrical interconnects and the working electrode are defined by printing a graphene flake-based ink (early designs of the array have interconnects based on a Ag-based ink); (ii) the Ag/AgCl electrodes, to be used as the pseudo-reference electrodes for glucose detection, and for reverse iontophoresis during glucose extraction, are defined by subsequent stages of printing of Ag- and AgCl-based inks, respectively.

Figure 5A:
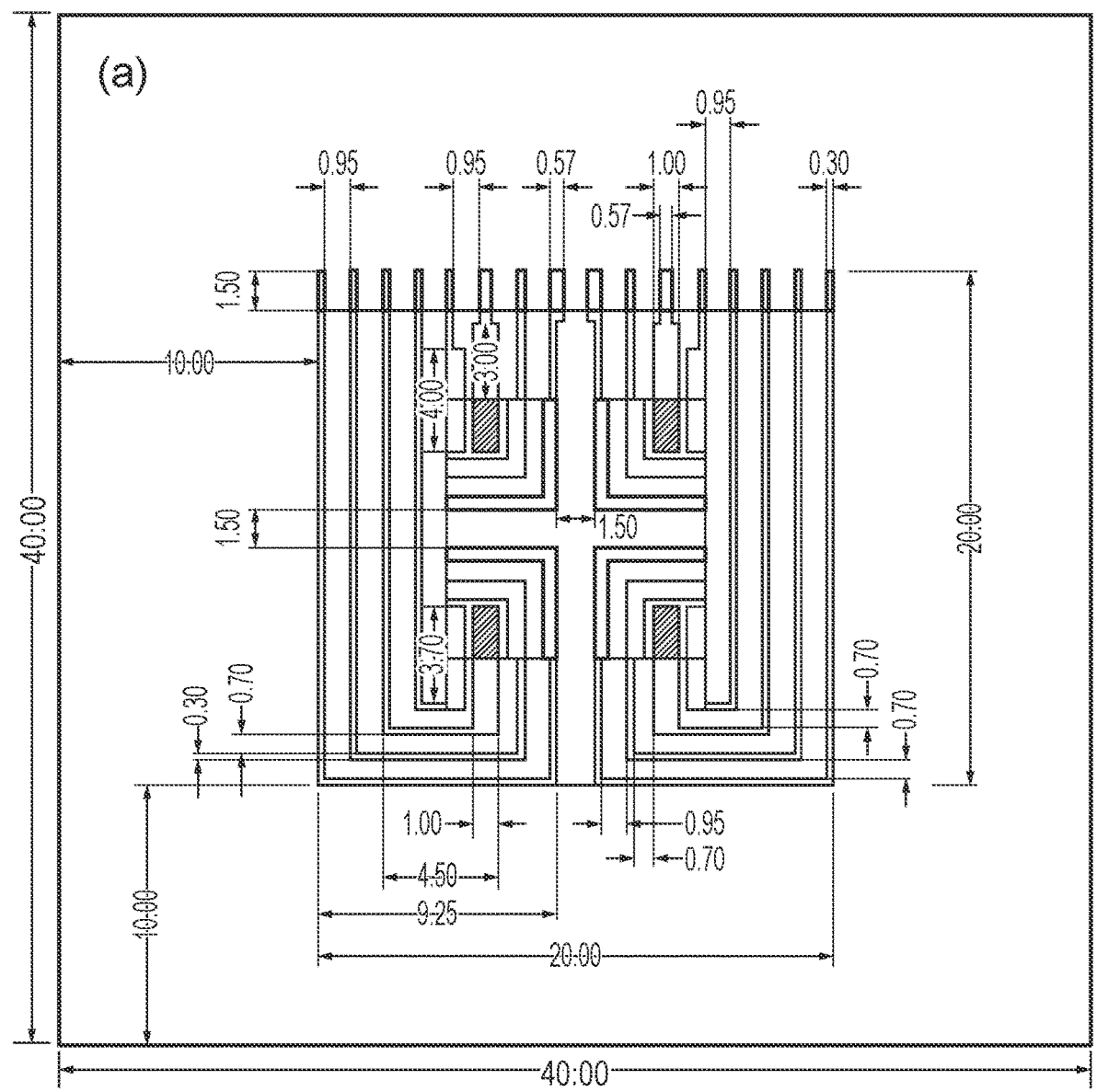
FIG. 5. Various schematic layouts of implemented 2×2 pixel arrays, with fully integrated planar (on-substrate) electrodes, with typical sizes indicated. Shapes of electrodes indicated are preferred, but other shapes, e.g. square or circular, may also be suitable. In this example, the active area of the pixel cell, including all electrodes (but excluding the interconnect tracks) is 3×3 mm$^2$. (a) Configuration 1: for glucose detection, the graphene/Pt NPs electrode (black) is the working electrode, while the small Ag/AgCl electrode (yellow) serves as both counter and reference electrode. The circuit used for glucose extraction is completely decoupled from the circuit used for detection, and formed between the largest Ag/AgCl electrode (yellow) and the Ag (green) electrode. (b) Configuration 2: graphene/Pt NPs (black) is now used for both working and counter electrodes (replacing the Pt electrode); while the Ag/AgCl electrode (yellow) has a dual function, serving as the reference electrode during glucose detection, as well as being one of the extraction electrodes which, in combination with the Ag electrode (green), form the glucose extraction circuit. Recycling of the Ag and AgCl content within the respective electrodes is obtained by reversing the polarity of the extraction current during a period of "recovery" that follows each extraction. (c) Configuration 3: Each pixel contains a working graphene/Pt NPs electrode, and two Ag/AgCl electrodes, a small one and a large one, which can play the role of reference and counter electrodes, respectively, while sensing the extracted glucose. In addition, reverse iontophoresis employs the largest of the Ag/AgCl electrodes located on two adjacent pixel devices as the anode and the cathode that form the extraction circuit. In this case, during one half of the operation cycle, glucose is extracted in one of the pixels, while in the second half of the operation cycle, the polarity of the extraction current is reversed, and glucose is extracted in the other pixel. In this way, the extraction and recovery of the AgCl content of each of the extraction electrodes involves sequentially two adjacent pixels, and not just a single pixel as in the configurations 1 and 2 above.
Figure 5B:
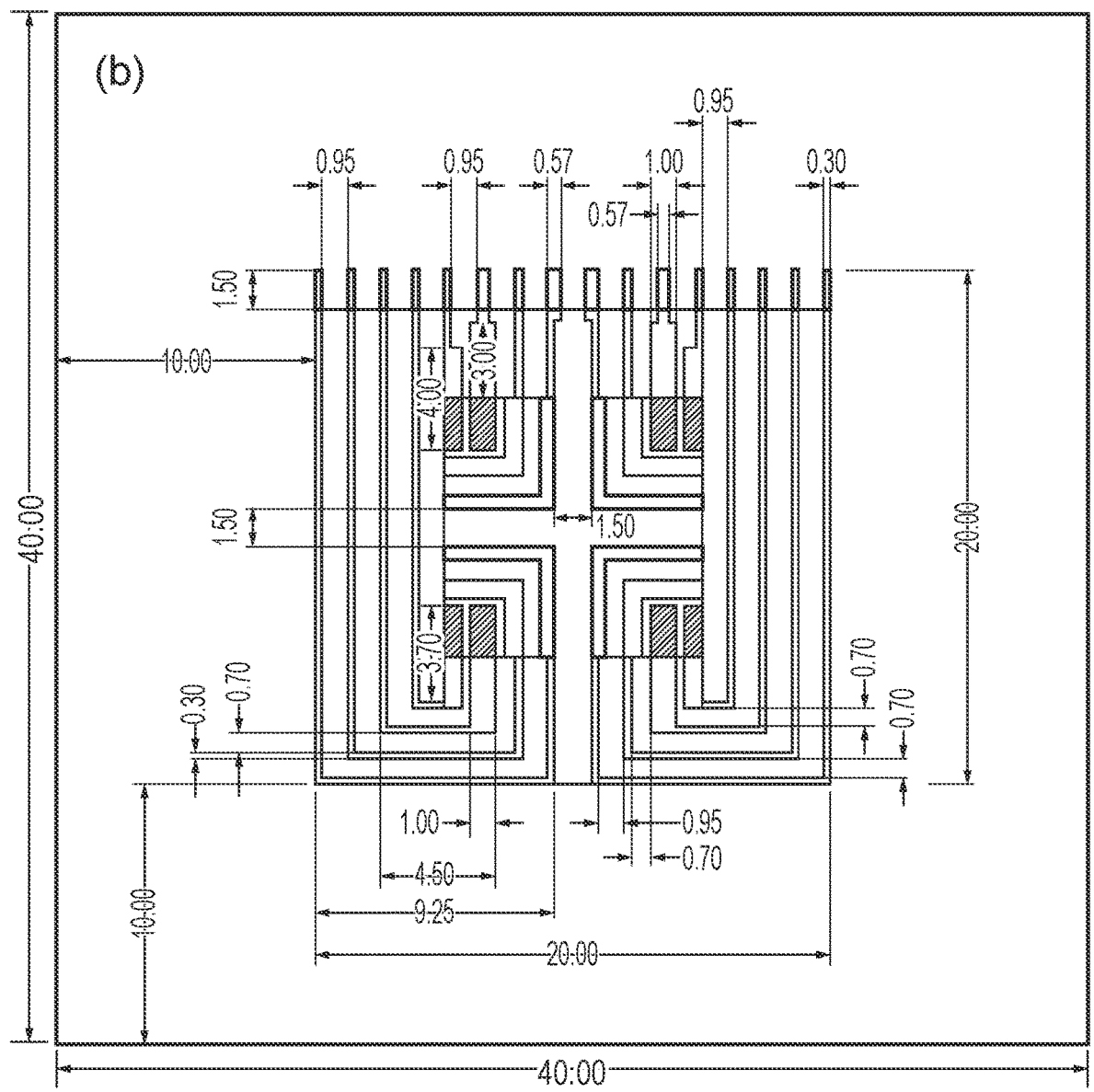
Figure 5C:
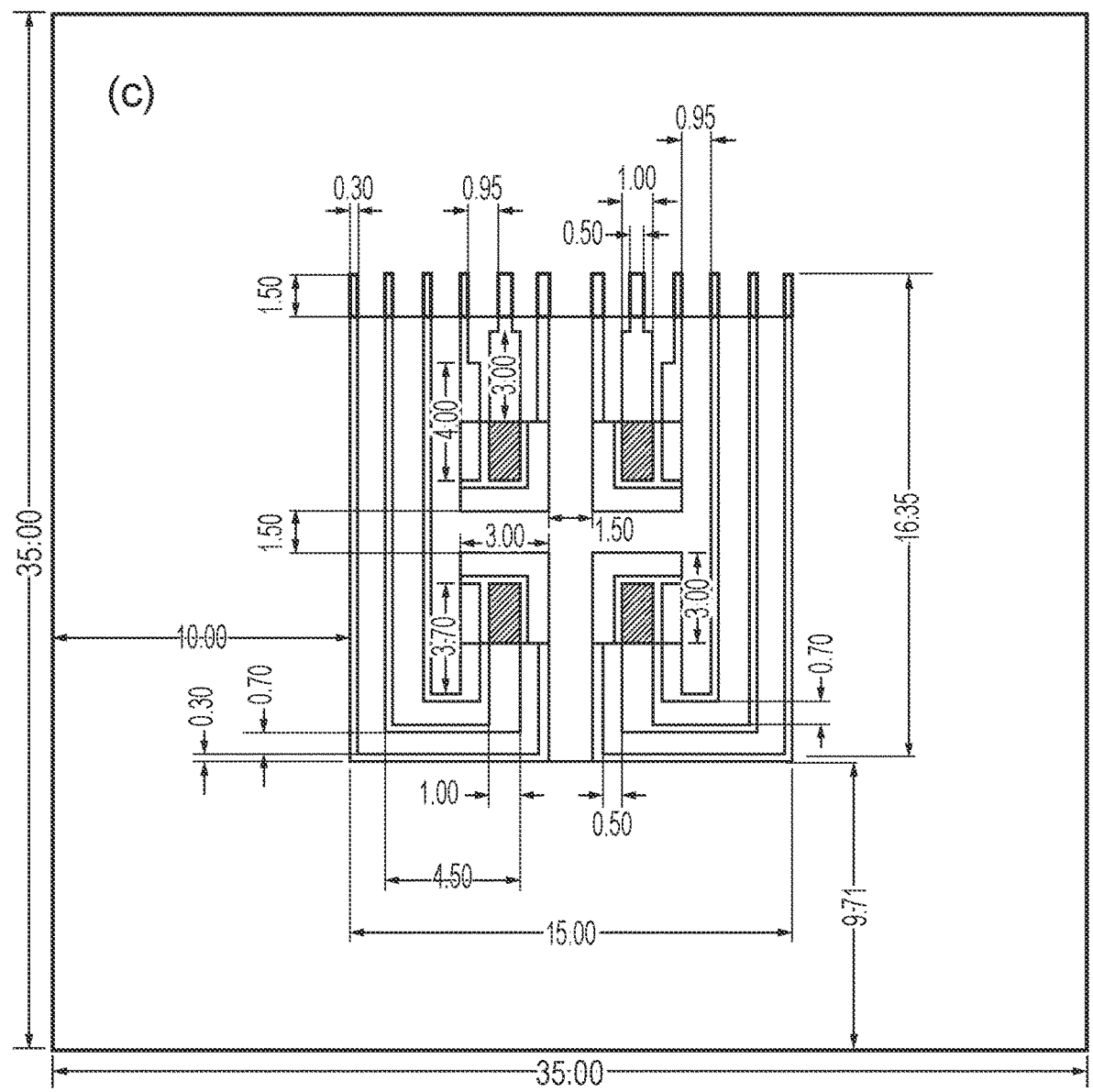

FIG. 5 illustrates the relative positioning of the various components of a 2×2 array: the spacing between the electrodes in a pixel is chosen so that the working and counter electrodes are close enough to the reference and iontophoresis electrodes in order to minimise the ohmic potential drop in solution, as well as to allow the extracted glucose to reach rapidly and efficiently the detection electrodes. Because the use of a single Ag/AgCl electrode for both extraction and detection (as proposed in the layout in FIG. 5(b)) may, in time, affect its performance, a second layout was designed in which the sensing and the reverse-iontophoresis circuits are entirely decoupled (i.e., they do not share any of the electrodes) (FIG. 5(a)). The design from FIG. 5(a), where only two electrodes are used for electrochemical detection, is a common strategy employed for low-current electrochemical sensing (Nature 2016, 529, 509-514, Anal. Chem. 2015, 87, 394-398).

Similar to step 5 of strategy 1, an insulating layer can be printed using an appropriate ink. Several such inks exist, including bio-compatible variants. The printed array is then coupled to the elastomer-hydrogel membrane, created using the same steps 6 to 8, as described above (Strategy no. 1).

Irrespective of the strategy used to fabricate the array, when using the layouts described in FIGS. 5(a) and 5(b) all the pixel devices in the array are expected to perform reverse iontophoresis extraction followed by electrode material "recovery" to avoid AgCl and Ag depletion within their respective electrodes during long term operation. For every pixel, this makes use of the Ag and AgCl electrodes that exist in each pixel. In contrast, the layout in FIG. 5(c) uses two adjacent pixel devices in the sequential extraction/recovery stages, so that at any given time only half of the pixels of the array extract glucose, while the other half only provide the AgCl electrodes needed for the completion of the extraction electrical circuit. Then, by reversing the polarity of the applied current, glucose is extracted in the next cycle of operation by the other half of the pixels of the array; the sequential recycling of Ag and AgCl between the respective pairs of pixel devices is thereby ensured. This sequential change in the polarity of the electrodes may also limit any polarization of the skin that has been suggested to be associated with stinging and erythema.

3. Proof of Principle

Examples of the miniaturised pixel devices of the present invention for non-invasive monitoring of transdermal glucose were tested to determine their detection range, limit of detection, specificity of response for glucose, and their ability to perform dual glucose extraction/detection through single follicular pathways. Additionally, the cross-talk between two adjacent pixel devices was also evaluated.

Figure 6A:
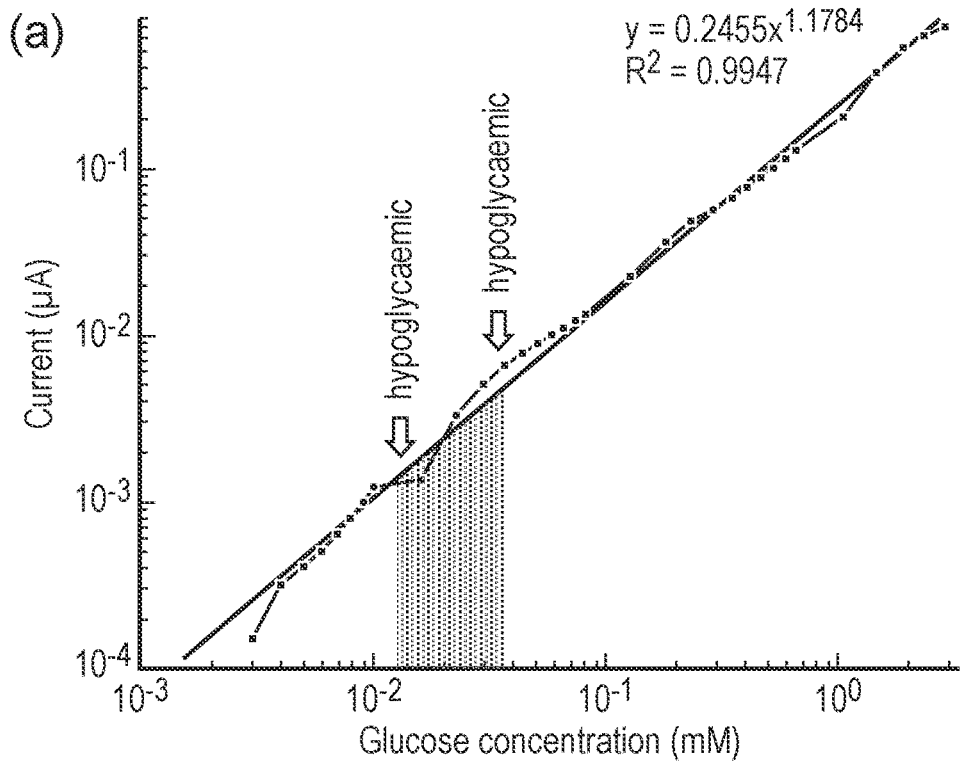
FIG. 6. (a) Full response curve of a typical graphene-based, electrochemical glucose sensor, obtained using Ag/AgCl and Pt wires as external electrodes. The hypo- and hyper-glycaemic limits within individual gel pixels of selected geometry are shown; this region of interest comfortably avoids the lower working limit of the sensor. (b) A similar response curve obtained with fully integrated, on-substrate electrochemistry electrodes. Inset: the linear response of the sensor over the 10-100 micromolar range, encompassing the hypo to hyper-glycaemic concentration limits. Measurements were acquired at 0.4V against a micro Ag/AgCl electrode.

FIG. 6(a) displays a typical electrochemical current versus glucose concentration calibration curve of a pixel device in an embodiment as realized via strategy no. 1. The pixel device was about 3 mm in diameter, and comprised an enzyme-encased gel reservoir of 24 μl containing 8 mg/ml glucose oxidase, and external (wire) Ag/AgCl and Pt electrodes in contact with the gel reservoir. The resulting calibration curve shows a single-law dependence over a concentration range from micromolar to more than millimolar, and displays a low limit of detection (LoD) of 4 micromolar. The hypo- to hyper-glycaemic range in diabetics (i.e., 3.5 to 12 mM in the blood, and of a quite similar range in the interstitial fluid), after dilution within the volume of the reservoir gel (24 μl), maps completely onto the sensor calibration curve; thus, with the geometric dimensions used in this example, the measured glucose concentration range is 10-40 micromolar, already well above the LoD of the sensor. These concentrations were reached with an extraction current of 0.2 mA applied over 1-hour extraction period. Further decrease in the volume of the gel reservoir displaces the sensor working range towards even higher concentrations and greater sensitivity.

Figure 6B:
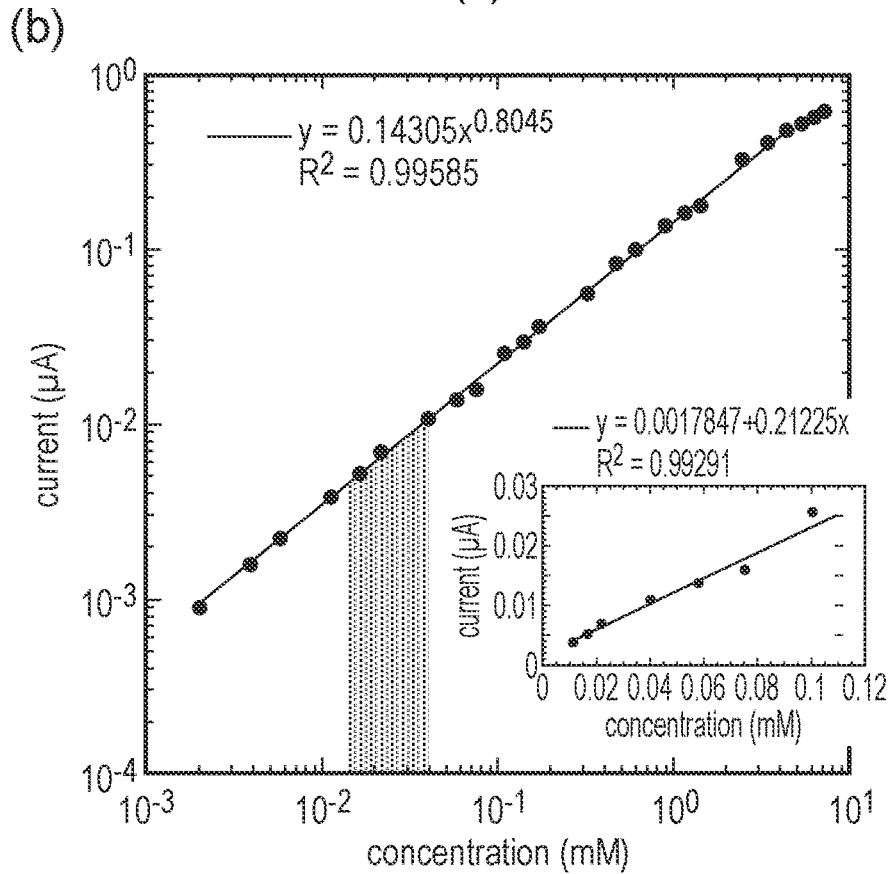

FIG. 6(b) displays the electrochemical current versus glucose concentration calibration curve of a full on-chip pixel device, where all the electrodes are planar and integrated with a PET substrate. The pixel device had a 4×2 $mm^2$ area, a gel reservoir of 10 μl containing 16 mg/ml glucose, and two planar electrochemistry electrodes made of platinum nanoparticle-decorated graphene and an Ag/AgCl film (see section 4, "Supporting Methods"), respectively. For this embodiment, a larger current was obtained at the lower glucose concentration end of the range than in the case of the embodiment corresponding to FIG. 6(a); this is most likely the result of the planar electrode geometry used, combined with a larger concentration of encased enzyme which can accelerate the initial rate of the enzyme reaction. A single-law dependence over the whole concentration range was found, and the limit of detection was found to decrease to below 2 micromolar.

In more recent experiments, the volume of the gel reservoir was decreased to about 1 μl, resulting in a thickness of about 0.1 mm, a most preferred value which greatly reduces the glucose diffusion time across the gel. This improvement allows one to decrease both the extraction time and extraction current, bringing these operation parameters of the device into the most preferred range.

Figure 7:
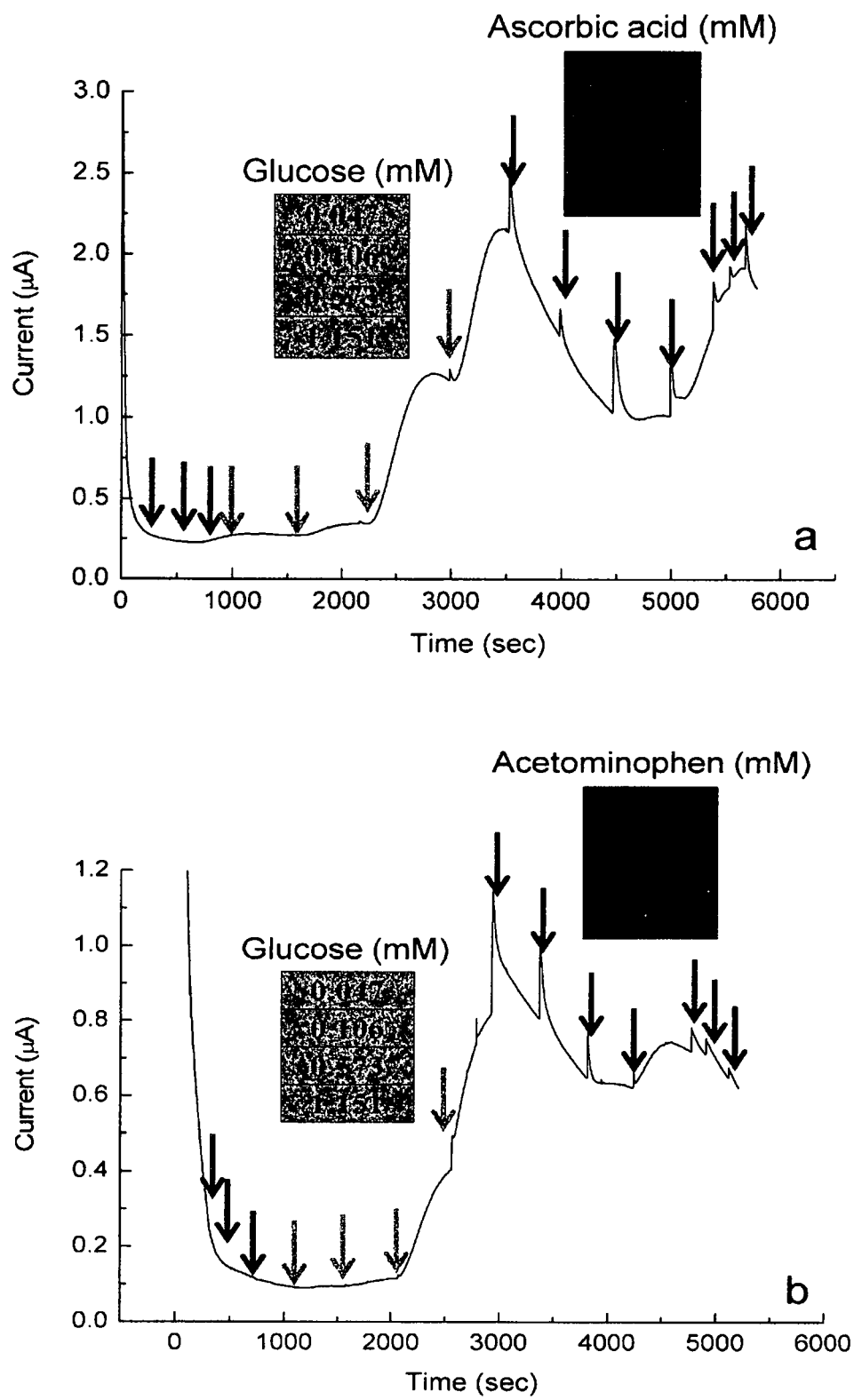
FIG. 7. Chronoamperometry in response to glucose entrapped in gel, upon addition of (a) ascorbic acid (indicated by purple arrows) and (b) acetaminophen (indicated by magenta arrows) Measurements were acquired at 0.4V against a micro Ag/AgCl electrode.

To demonstrate the specific response to glucose, the pixel detector was exposed to ascorbic and uric acids, and to acetaminophen, potentially interfering species that may be present in addition to glucose in the iontophoretic extract. FIG. 7 shows that the plateau of the amperometric current increases after each glucose addition, and decreases when either of the possible interferants are added. This is consistent with dilution of the glucose already present in the gel, and shows that the sensor is essentially insensitive to species that do not interact specifically with the immobilized enzyme.

The glucose extraction function of the platform was shown by performing reverse iontophoresis (RI) ex vivo in simple diffusion cells using porcine skin (see section 4, "Supporting Methods"), which is an excellent model for the human counterpart (Schmook, F. P., J. G. Meingassner, and A. Billich, *Comparison of human skin or epidermis models with human and animal skin in in-vitro percutaneous absorption*. International Journal of Pharmaceutics, 2001. 215(1-2): p. 51-56). As mammalian skin carries a net negative charge at pH 7.4, electro-osmotic transport occurs in the direction of cation migration (Marro, D., et al., *Contributions of electromigration and electroosmosis to iontophoretic drug delivery*. Pharm Res, 2001. 18(12): p. 1701-8). In these experiments, a current of 0.2 mA was applied over a 1-hour extraction time. Successful reverse iontophoretic (RI) sampling of glucose, when present in the sub-dermal solution at different concentrations, is demonstrated by the chronoamperometric current measured in the gel (FIG. 8) and then converting this current to a glucose concentration using a calibration curve of the type shown in FIG. 6. A negative control RI experiment, performed when no glucose was present in the sub-dermal solution, confirmed that no interfering contribution from the skin itself was evident. Furthermore, the electrochemical detection of glucose in the pixel device was independently validated by quantitative $^1$H-nuclear magnetic resonance ($^1$H-qNMR), as discussed below. As mentioned in the section entitled "Geometry considerations", with an elastomer membrane of 0.1 mm thickness and gel contained therein of 2 mm diameter, the gel volume decreases by a factor of ~60, allowing both the extraction period and the applied RI current be reduced to typically 10-15 minutes and 0.02 mA, respectively, while maintaining the glucose concentration in the gel comfortably within the detection range.

Figure 8:
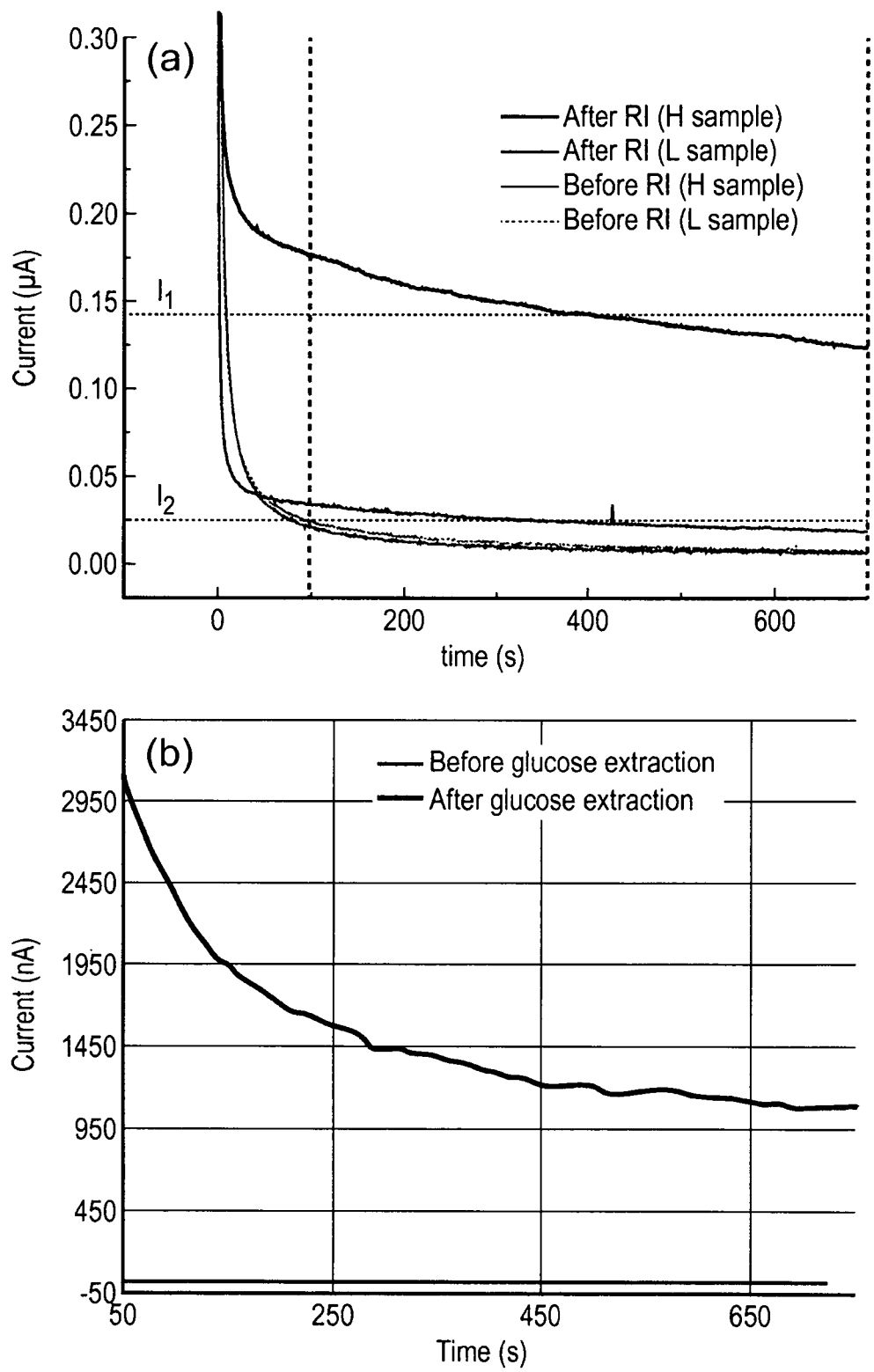
FIG. 8. Detection of ex-vivo RI-extracted glucose via chronoamperometry. (a) Experiment using Ag/AgCl and Pt wires as external electrodes. The same miniature graphene sensor was used as the working electrode and for comparing skin samples with substantially different hair densities: chronoamperometric current baselines were recorded before RI (black and light blue curves), and after RI involving "single-hair targeted" extraction (red curve), using a skin sample with 32 hairs/cm$^2$ (labelled as H), and the other, through non-follicular skin (dark blue curve), using a skin sample with only 6 hairs/cm$^2$ (labelled as L). (b) Glucose extraction demonstrated using planar electrodes on a PET substrate.
Figure 9:
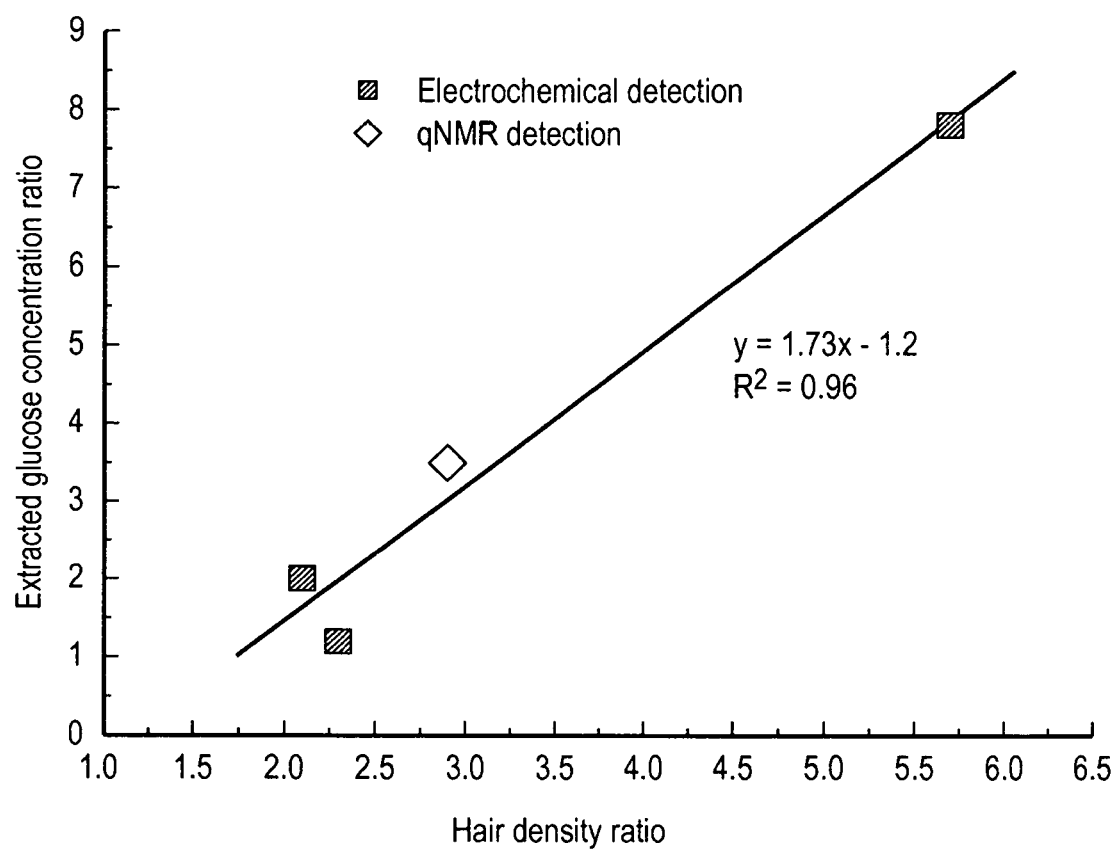
FIG. 9. Correlation between extracted glucose concentration and hair density ratios, combining results obtained via either chronoamperometric or quantitative NMR detection. Each data point represents a different extraction experiment. The results from both techniques lie on the same "glucose concentration versus hair density" curve, indicating self-consistency between electrochemical and NMR assays of glucose, with the latter providing validation of the former.

The preferential RI extraction of glucose through the hair follicles was established in two experiments, as shown in FIG. 8(a): first, via hair "targeting", where the miniature elastomer-supported gel "pixel" was positioned directly on a single hair follicle and, second, through the comparison of extraction across skin samples of varying hair density. In both experiments, RI was conducted under identical conditions on two skin samples with different hair densities; identical gel reservoir volumes were used and the electrochemical detection of glucose therein was performed with the same graphene sensor. Single-follicle, hair-"targeted", preferential extraction, performed on a skin sample with 34 hairs/cm$^2$, was contrasted with that from another that was relatively devoid of follicles, with only 6 hairs/cm$^2$ (FIG. 8) The results from these measurements permitted the relative magnitudes of the RI extraction fluxes via follicular and non-follicular pathways to be estimated. When the sub-dermal concentration of glucose was 10 millimolar, the flux via the preferential pathways was 3.5 nmol·mA$^{-1}$·hr$^{-1}$, whereas that across non-follicular skin was 0.4 nmol·mA$^{-1}$·hr$^{-1}$. These values are consistent with the overall glucose extraction flux (4.5 nmol·mA$^{-1}$·hr$^{-1}$) reported earlier across porcine skin ex vivo (Sieg, A., R. H. Guy, and M. B. Delgado-Charro, *Electroosmosis in Transdermal Iontophoresis: Implications for Noninvasive and Calibration-Free Glucose Monitoring*. Biophysical Journal, 2004. 87(5): p. 3344-3350). The preferential pathway contrast is also in agreement with the enhanced iontophoretic flux of hydroquinone at hair follicles determined by direct visualization and quantification of electro-osmosis using scanning electrochemical microscopy (Bath, B., H. White, and E. Scott, *Visualization and Analysis of Electroosmotic Flow in Hairless Mouse Skin*. Pharmaceutical Research, 2000, 17(4): p. 471-475). FIG. 9 collects the results of several experiments in which the efficiency of glucose extraction was correlated with hair density, and the analyte was detected either electrochemically or by $^1$H-qNMR. The data, which show a clear correlation between the ratios of concentrations extracted through follicle-rich and follicle-poor skin samples and the respective hair density ratios thereof, demonstrate that glucose extraction by RI into the miniature "pixels" indeed occurs primarily through preferred follicular pathways. The excellent agreement between the amperometric and NMR analytical techniques provides further confidence in the dual extraction-detection functions of the pixel device.

FIG. 8(b) demonstrates reverse iontophoresis employing planar electrodes fully integrated with a PET substrate. The trend of the data is very similar to the ones described in FIG. 8(a).

Figure 10:
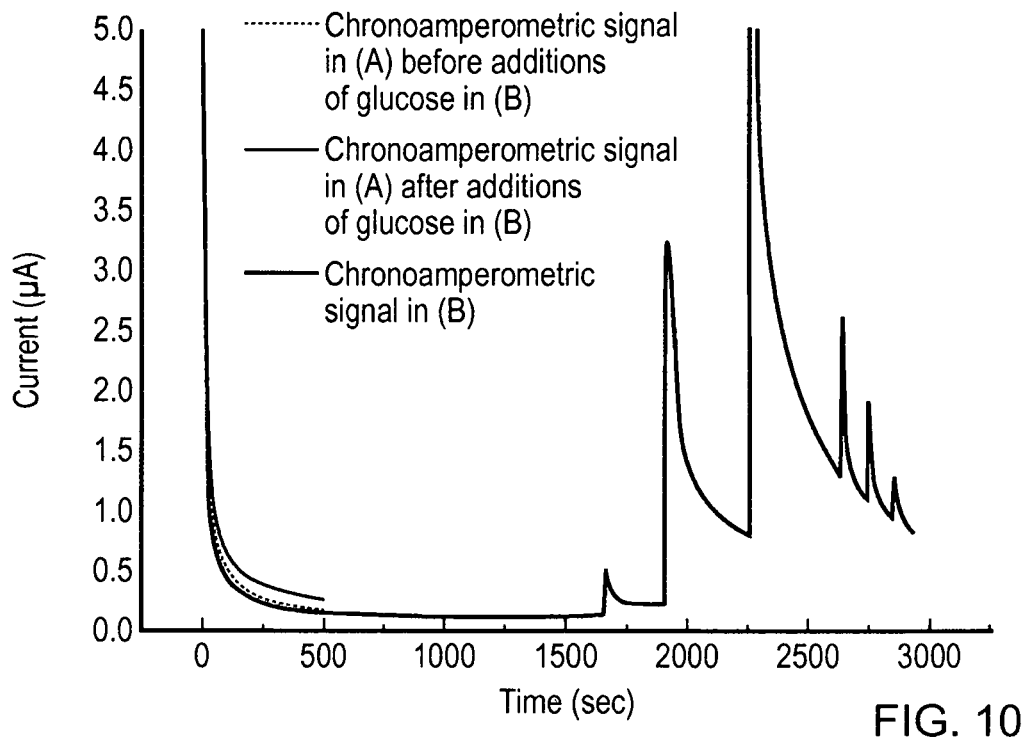
FIG. 10. Absence of cross-talk between two adjacent device pixels, A and B, by chronoamperometry. The two pixels are constructed on a contiguous graphene film, but have individual gel reservoirs. Pixel B was subjected to glucose additions in the 10 μM to 1 mM range. The baseline response in the adjacent pixel A, not exposed to glucose, was found to increase by no more than 3% of that corresponding to the total amount of glucose added to pixel B.
Figure 11:
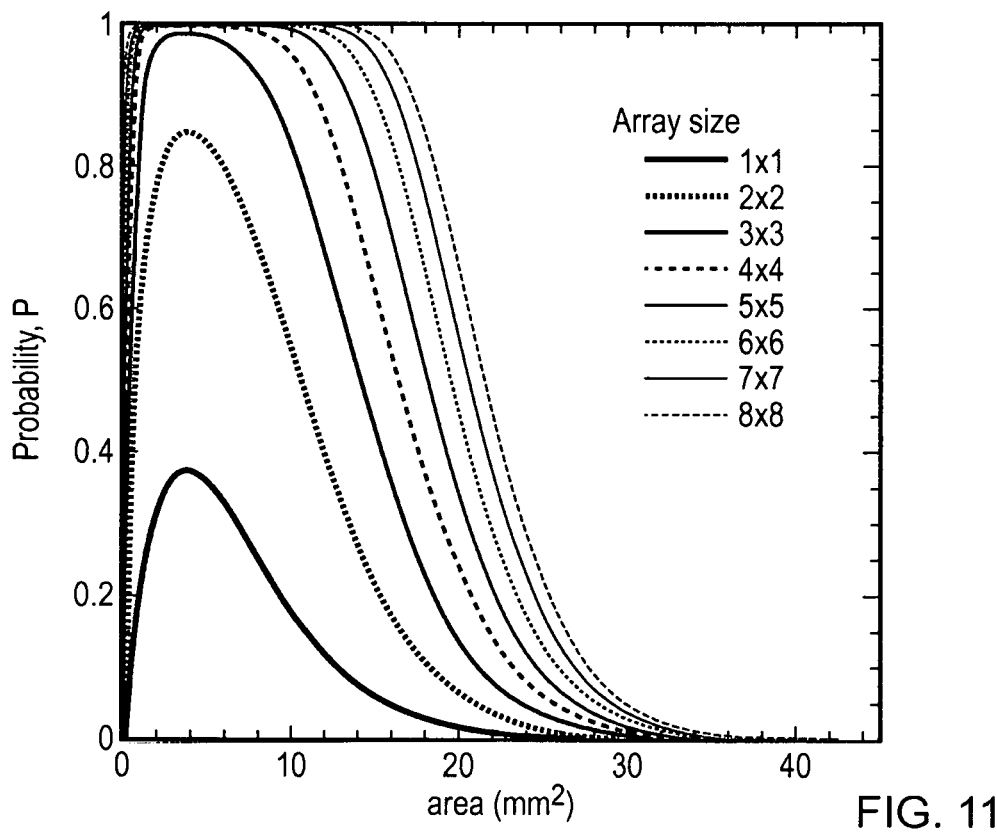
FIG. 11. Probability P that the pixel array has at least one working pixel with just a single pathway per pixel (calculated at 27 follicles/cm$^2$; i.e. the median value across the entire typical follicular density range in humans), as a function of pixel active area and for various numbers of pixels in the array. Here, the active area is defined as the pixel device area through which glucose extraction takes place, coinciding with the footprint area of the gel reservoir. A pixel active area of 2 to 6 mm$^2$ maximises the probability of hitting a single follicle in a randomly-positioned, untargeted measurement.
Figure 12:
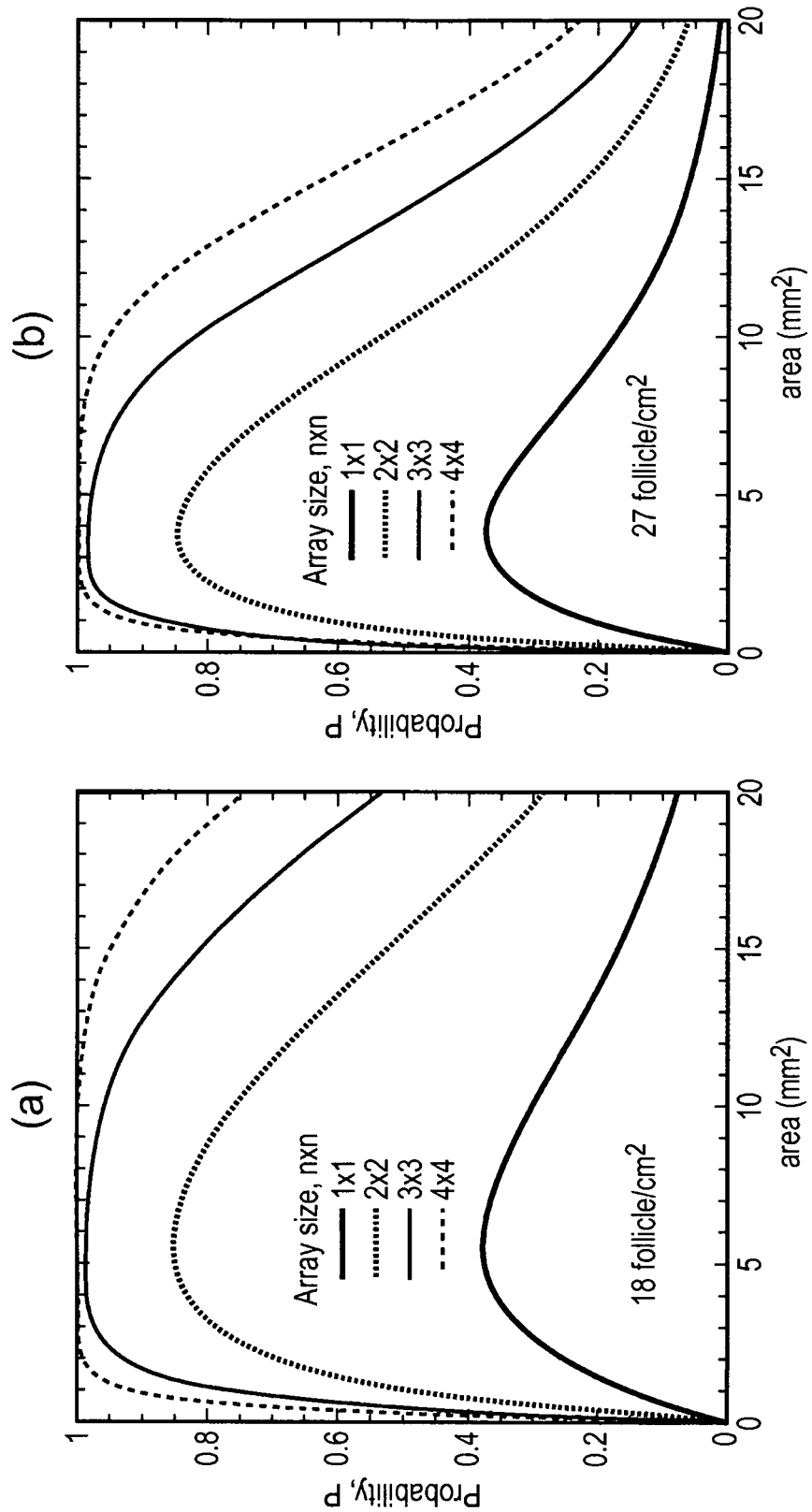
FIG. 12. (a-d) Probability P, as a function of pixel active area and for different sized arrays, that an array device with n×n pixels (where n=1-4) has at least one working pixel when applied to skin with (a) 18, (b) 27, and (c) 36 follicles/cm$^2$. A working pixel is defined as a pixel for which there is just a single follicle 'hit' (i.e. the opposite of a non-working pixel, for which there is either no or more than one follicle 'hit'). (d) P as a function of pixel active area for a 4×4 array for all three selected follicle densities, showing that an overlapping range of a values, i.e. 2-5 mm$^2$, exists for all typical human follicular densities on the ventral forearm. This subsequently informs the design of a working array.
Figure 12:
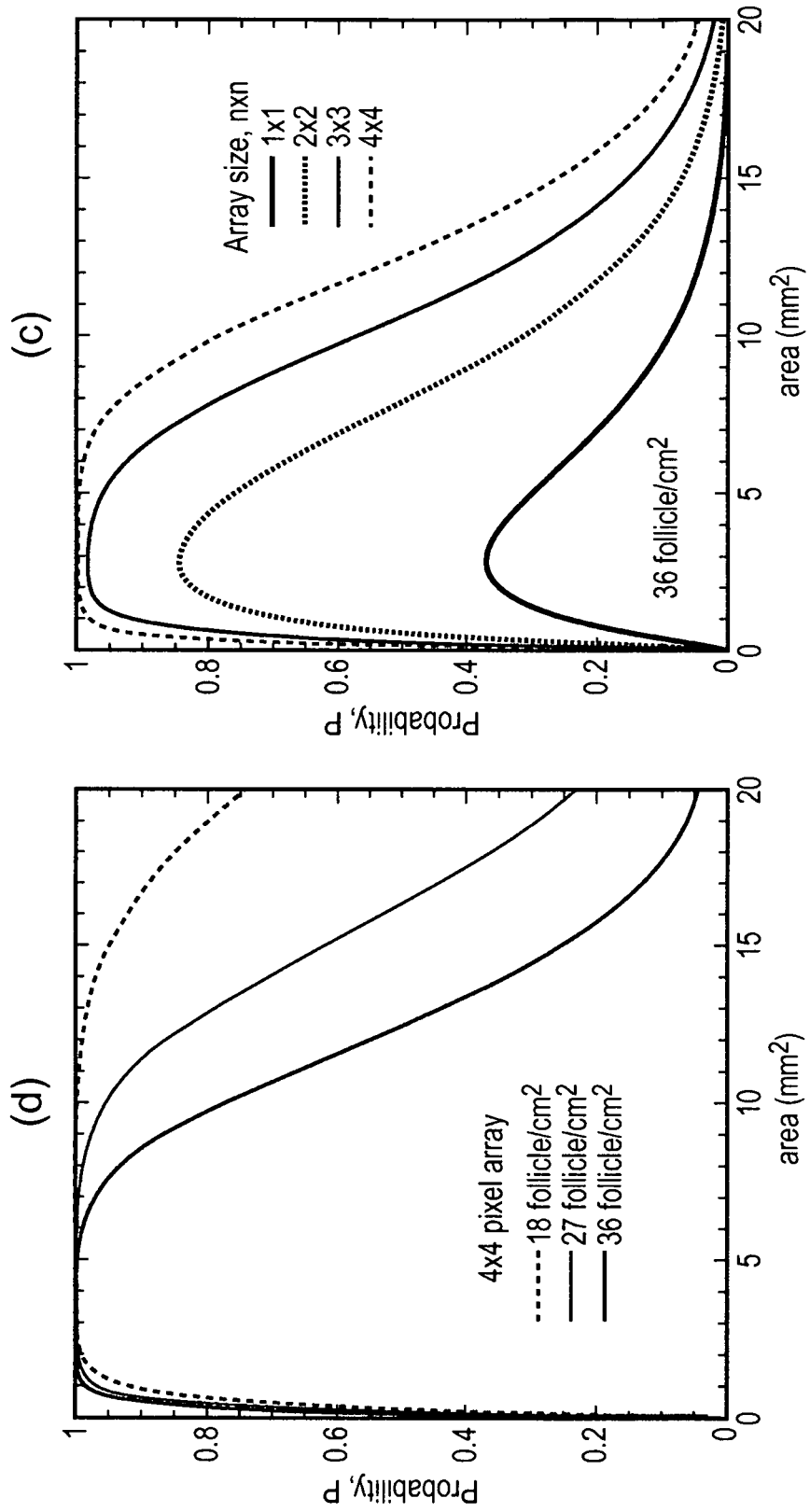
Figure 13:
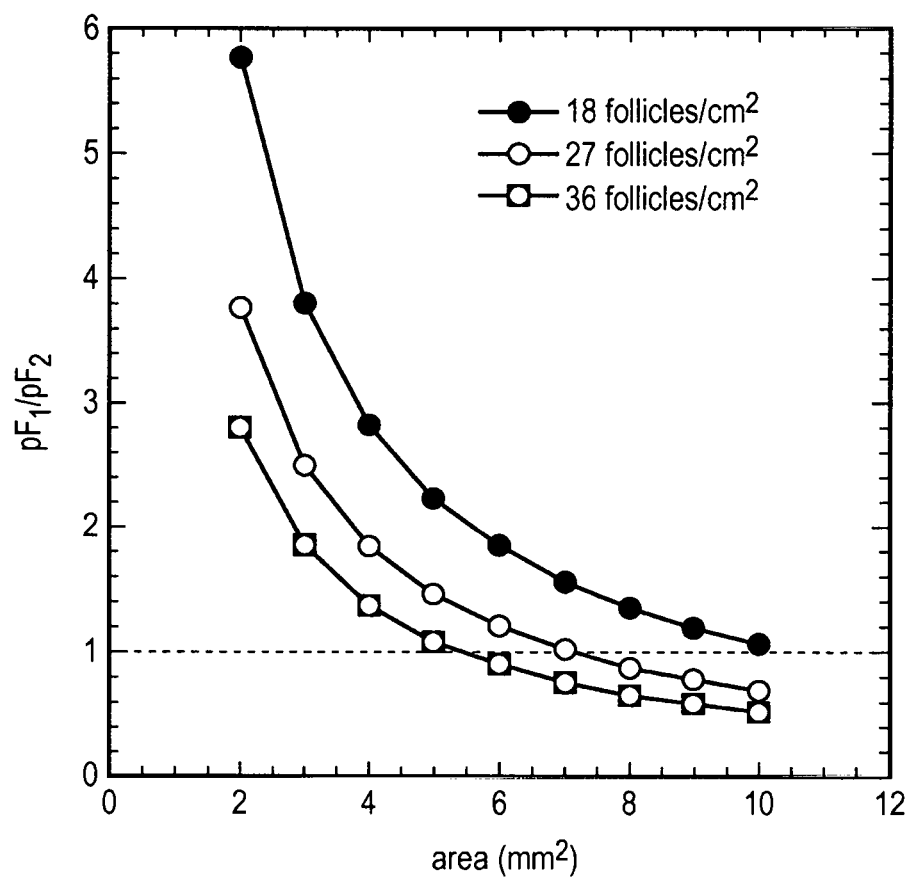
FIG. 13. Ratio of probabilities $pF_1/pF_2$ as a function of pixel active area for 18, 27, and 36 follicles per cm$^2$; where $pF_1$ is the probability that a single follicle is hit by a pixel of active area a, while $pF_2$ is the probability that two follicles are hit by a pixel of active area a. When the pixel area a is 2-5 mm$^2$, the probability $pF_1$ of a pixel hitting a single follicle dominates, over all typical follicular densities; the smaller the value of a, the greater the probability of single follicle hits.

Negligible interference between adjacent "pixel" devices was also demonstrated (FIG. 10). Two "pixel" reservoirs containing enzyme were incorporated into an elastomer matrix and separated by about 1.5 mm. The "pixels" were positioned over a single, continuous graphene sensor the area of which was double that of a single "pixel". This created two devices coupled through the graphene film, which acted as the working electrode in the electrochemical reaction, but decoupled in terms of the enzyme reaction taking place in the two separate hydrogel reservoirs. Chronoamperometry was first performed on one of the "pixels", the reservoir of which contained no glucose, and a control, baseline response was obtained. The chronoamperometric current in the second "pixel" was then measured before and after additions of glucose at various concentrations from 10 micromolar to 1 millimolar. Lastly, the chronoamperometric response in the first "pixel" was re-determined to assess any cross-talk between the two devices. It was found that the baseline response in the first "pixel" increased by no more than 3% of that corresponding to the total amount of glucose added to the second "pixel". In other words, even with a graphene electrode common to both devices, the use of individual hydrogel reservoirs effectively decouples the response of the individual "pixels". Achieving complete decoupling is anticipated in a practical embodiment of the array for which individual graphene detectors are envisaged.

4. Supporting Methods

Detection Device Fabrication. Materials Processing.

Graphene-Based Sensor Fabrication.

Chemical vapour deposition (CVD) graphene squares, of 3×3 or 2×2 mm$^2$, originally synthesized on Cu foils, were transferred onto SiO$_2$/Si (in early experiments) or flexible PET substrates by standard procedures (Bae, S., et al., *Roll-to-roll production of 30-inch graphene films for transparent electrodes*. Nat Nano, 2010. 5(8): p. 574-578). Electrical interconnects to graphene on SiO$_2$/Si were enabled by successive deposition of Ti and Au tracks (e.g., 10/60 nm thick, respectively), where Ti served as an adhesion layer for the Au film; in the case of graphene on PET, electrical interconnects were made out of Ag which adheres to PET directly. These metallic interconnects were later replaced with graphene itself. Pt nanoparticles were then electrochemically deposited onto the graphene squares, creating the hybrid graphene/Pt NPs pixel material used as the working electrode during electrochemical glucose detection. Within a pixel device, the graphene area used in electrochemistry was then insulated from the rest of the electrical circuit with a polydimethylsiloxane (PDMS) or silicone rubber frame with a central cylindrical hole, into which the hydrogel reservoir was cast on top of the graphene. The electrochemistry circuit was completed (i) with external Ag, Ag/AgCl and Pt wires in the early experiments, and (ii) with chip-integrated Ag/AgCl (and Pt, in some variants) electrodes in later embodiments.

External Reference Microelectrode.

An Ag/AgCl micro-electrode was fabricated by coating a 99.95% pure, silver wire with AgCl by chronoamperometry in a 3.5 M KCl solution, with Pt as reference and counter electrodes, for 1 hour at 1 V. The wire was then encased in a 1% w/v agarose gel containing 0.1 M KCl. The electrode held only a low (0.1 M) KCl concentration to limit the amount of glucose oxidase inhibitor present. The electrode was stored in 0.1 M KCl at 4° C. when not in use, and its performance and stability over time were confirmed periodically using cyclic voltammetry.

Chip-Integrated Electrochemistry Electrodes.

To fabricate a fully integrated sensor, all electrodes involved in electrochemistry were defined directly on the substrate. As indicated in FIG. 5, this necessitated creation of Ag/AgCl electrodes.

Thermal/e-beam evaporation: Firstly, Ag patterned regions of 850 nm thickness were deposited directly on PET using stencil masks. Note that on other substrates, such as $SiO_2$, which were used for proof-of-principle studies, a layer of 5-10 nm of Ti was first deposited in order to ensure adhesion of the Ag layer. Then, an additional AgCl layer of about 300 nm in thickness was deposited on top of the Ag regions to create a stable AgCl/Ag reference electrode. Such thick layers of Ag and AgCl are needed to ensure a long lifetime of the reference electrode (B. J. Polk et al., Sensors and Actuators B 114 (2006) 239-247).

Chemical and electrochemical methods: (i) chemically, a 50 mM $FeCl_3$ solution is applied to the Ag surface for 20 seconds at room temperature, followed by rinsing with de-ionized water; (ii) electrochemically, AgCl was produced by chrono-amperometry in a 1M KCl solution with an on-chip Ag electrode as the working electrode, and Pt wires as reference and counter electrodes, followed by rinsing with de-ionized water.

Nernstian behaviour was obtained in solutions of various chloride ion concentration independent of the preparation route of the AgCl/Ag electrode.

Printing technologies: Ag/AgCl electrodes can also be created using direct printing of stacked layers of Ag- and AgCl-based inks.

Gel Casting and Enzyme Entrapment.

12 μL of an 8 mg/mL solution of glucose oxidase was deposited directly onto a graphene sensor region of 2 or 3 mm diameter as defined by the PDMS or silicone rubber frame. A clear 1% w/v solution of low temperature gelling agarose in 0.1M phosphate buffer pH 7.4 was prepared by warming the mixture above 80° C. and then cooling to 28° C.; i.e., below the gelling temperature of ~36° C. Then, 12 μL of the gel (still at 28° C.) was added to the enzyme solution, such that the enzyme's catalytic and structural properties were maintained (Zoldák, G., et al., *Irreversible Thermal Denaturation of Glucose Oxidase from Aspergillus niger Is the Transition to the Denatured State with Residual Structure*. Journal of Biological Chemistry, 2004, 279(46): p. 47601-47609) and enabling its efficient entrapment in the gel.

In order to reduce the extraction current and the time period, the volume of gel needs to be decreased (see section entitled "Geometry considerations"). Hence, 2 μl enzyme-containing gel was cast into the holes (1.5-2 mm diameter) of a 0.1 mm thick PDMS membrane. In general, the volume of enzyme-containing gel scales down with decreasing volume defined by the thickness of the supporting elastomer membrane and the dimensions of the reservoir holes within.

The use of other types of hydrogel, with a gelling temperature below the denaturation point of the enzyme, may allow direct mixing of the enzyme with the hydrogel, and then direct injection of the mixture into the holes of the elastomer membrane.

Deposition of Platinum Nanoparticles. Electrochemical Method:

A cyclic voltammogram acquired in 10 μL of 0.1M $H_2SO_4$, 1.7 mM hydrogen hexachloroplatinate, at 20 mV/sec scan rate, shows a typical chloride reduction peak at about −0.35V against a micro Ag/AgCl reference electrode.

Sputtering:

DC sputtering under argon was performed with a base pressure better than $9 \times 10^{-7}$ mbar. A nominal thickness of 10 nm of Pt was deposited resulting in particle sizes of 3 to 5 nm in diameter. This method may be suitable for large scale production.

Reverse Iontophoresis (RI), Ex Vivo (on Pig Skin). Output Data. Material Preparation.

Abdominal pig skin was obtained from a local abattoir, dermatomed to a nominal thickness of 750 μm, frozen within 24 hours of slaughter and thawed before use. Its follicular density was determined by inspection under an optical microscope. 10 and 100 mM D-glucose solutions (in deionized, MilliQ-water) were prepared in full-strength PBS and left to mutarotate overnight for use as the subdermal solutions for RI. The amount of chloride needed to fulfil the demands of the electrochemical reaction was estimated to be 0.9 mM, which is well within the range supplied by the PBS used for the glucose solutions.

Transdermal RI Glucose Extraction.

A piece of skin separated the two halves of a vertical Franz diffusion cell, with the epidermal side facing the upper compartment. The lower, sub-dermal chamber of the cell was filled with 7.5 mL of either 10 or 100 mM glucose solution, and magnetically stirred for 1 hour. RI extraction was performed in two experimental configurations: (i) first, with external wire extraction electrodes, and then (ii) with chip-integrated extraction electrodes.

External Electrodes:

The enzyme-containing gel reservoir was positioned on the skin surface with the Ag/AgCl porous cathode contacting the "pixel". A silver anode was inserted into the sub-dermal compartment. As the two electrodes were therefore located on opposite sides of the skin, the electrical resistance of the iontophoresis circuit was about one-half of that expected in vivo, where both electrodes would be located on the skin surface and the iontophoretic current must, as a consequence, cross the skin twice. However, because RI extraction is undertaken at constant current, the only difference between the in vitro and in vivo situations is the approximately two-fold higher voltage required to drive the current used in the latter case (Potts, R. O., *Mechanisms of Transdermal Drug Delivery*. 1997: Taylor & Francis). RI was performed by passing a constant current of 0.2 mA for 1 hour between the anode and cathode from a power supply; the potential across the skin was monitored regularly during current passage. The RI current application time employed permitted the extracted glucose to distribute essentially homogenously across the entire thickness of the gel reservoir.

Chip-Integrated RI Electrodes:

An on-chip Ag and Ag/AgCl pair of electrodes was created via identical methods to those described above for the fabrication of on-chip electrochemistry electrodes.

Output Data of the Device:

The chronoamperometric current (FIG. 9) was recorded, typically, for 700 seconds in each measurement, then averaged over the last 600 seconds of the total measurement period (i.e., corresponding to the plateau region), and the corresponding background value (i.e., before RI) subtracted.

Pixel Array on a Flexible Substrate: Characteristics and Operation

1. Proof-Of-Principle

Figure 14:
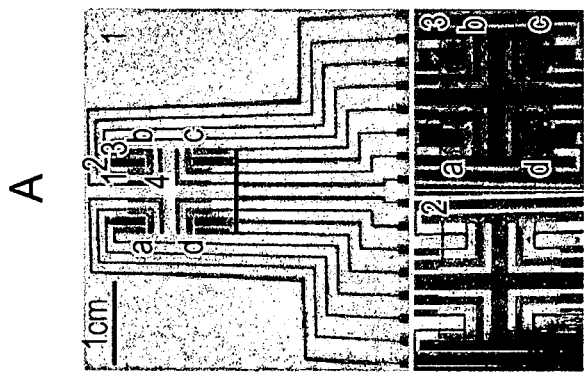
FIG. 14. A functional, fully integrated, graphene-based 2×2 pixel array on a flexible substrate. (a) Realization of a graphene-based 2×2 pixel array on a flexible (PET) substrate. Panel 1: Complete layout of the array. The prototype comprises electrodes for extraction-detection, sensing regions (Pt nanoparticle-decorated graphene of 2 mm$^2$ each), and an elastomer membrane with perforations (panel 2) within which a glucose-encasing hydrogel was deployed forming extraction regions of about 6 mm$^2$ each (dashed contours, panel 3). Only electrodes 1 to 3 participate in extraction-detection, while electrode 4 plays no role in this experimental configuration. (b-c) 10 mM subdermal glucose was extracted across porcine skin ex vivo for 5 minutes under ~0.5 mA/cm$^2$ RI current. (b) Panel 1: Sensitivity calibration curves for the 4-pixel sensor devices, demonstrating very similar current-concentration dependencies (slightly supra-linear power laws). The targeted concentration operational range is indicated in purple. Panel 2: Detected current versus time after glucose extraction within each of the four pixels characterized in panel 1; the number of follicles targeted by each of the pixels is indicated. Extraction of non-glucose containing PBS is also shown as a negative control (black baseline). Panel 3: Detected current versus time measured after two successive extractions using the same pixel device: subdermal glucose concentrations were 10 and 100 mM, respectively. Concentrations of extracted glucose are determined from the respective calibration curve of the device, and agree with calculations based on the follicular extraction flux and the number of follicles probed. (c) Panels 1 and 2 show an example of visual correlation between the number of follicles (~28 follicles/cm$^2$ in this case) probed by each array pixel (6 mm$^2$ extraction area, dashed contour) and the current detected after extraction. The array electrodes are visible through the skin.
Figure 14:
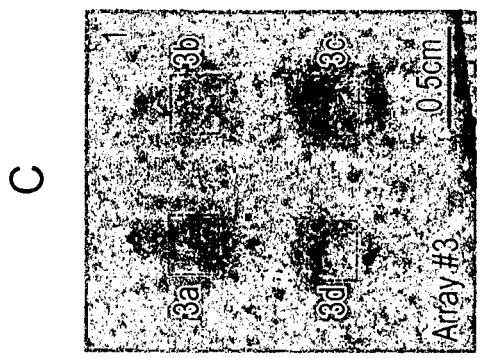
Figure 14:
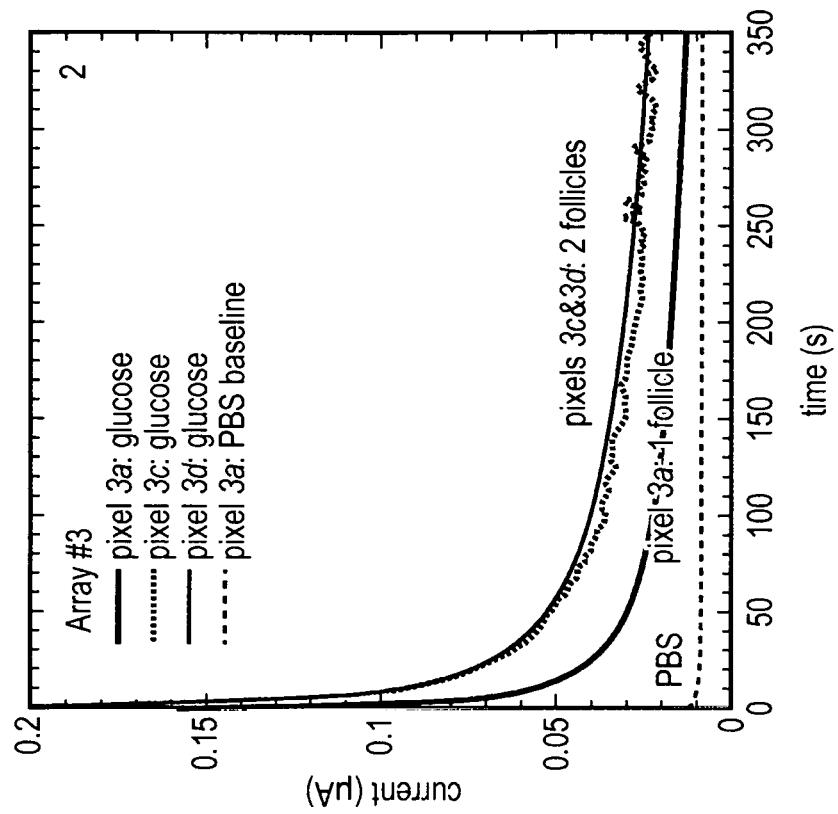
Figure 14:
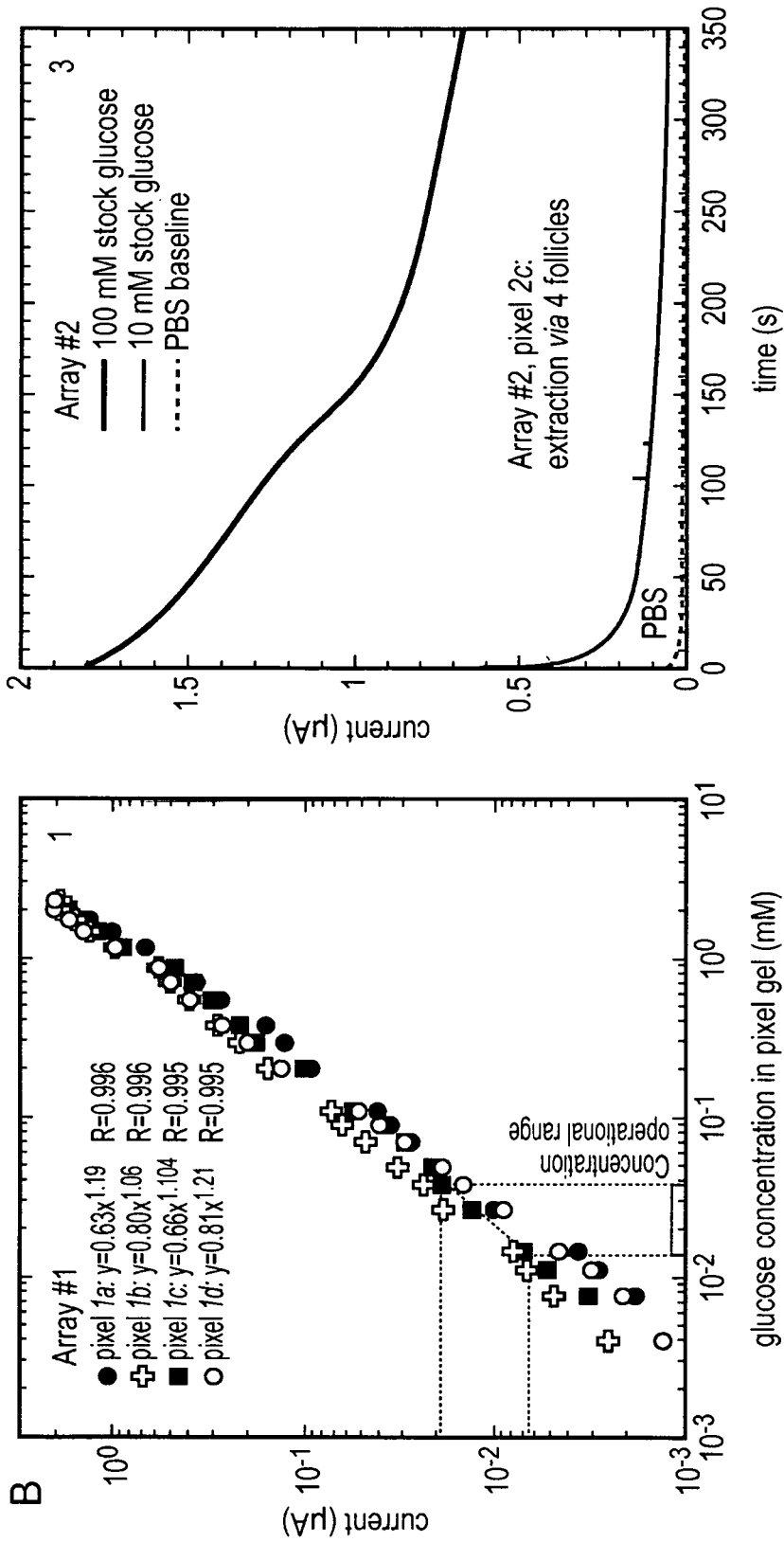
Figure 14:
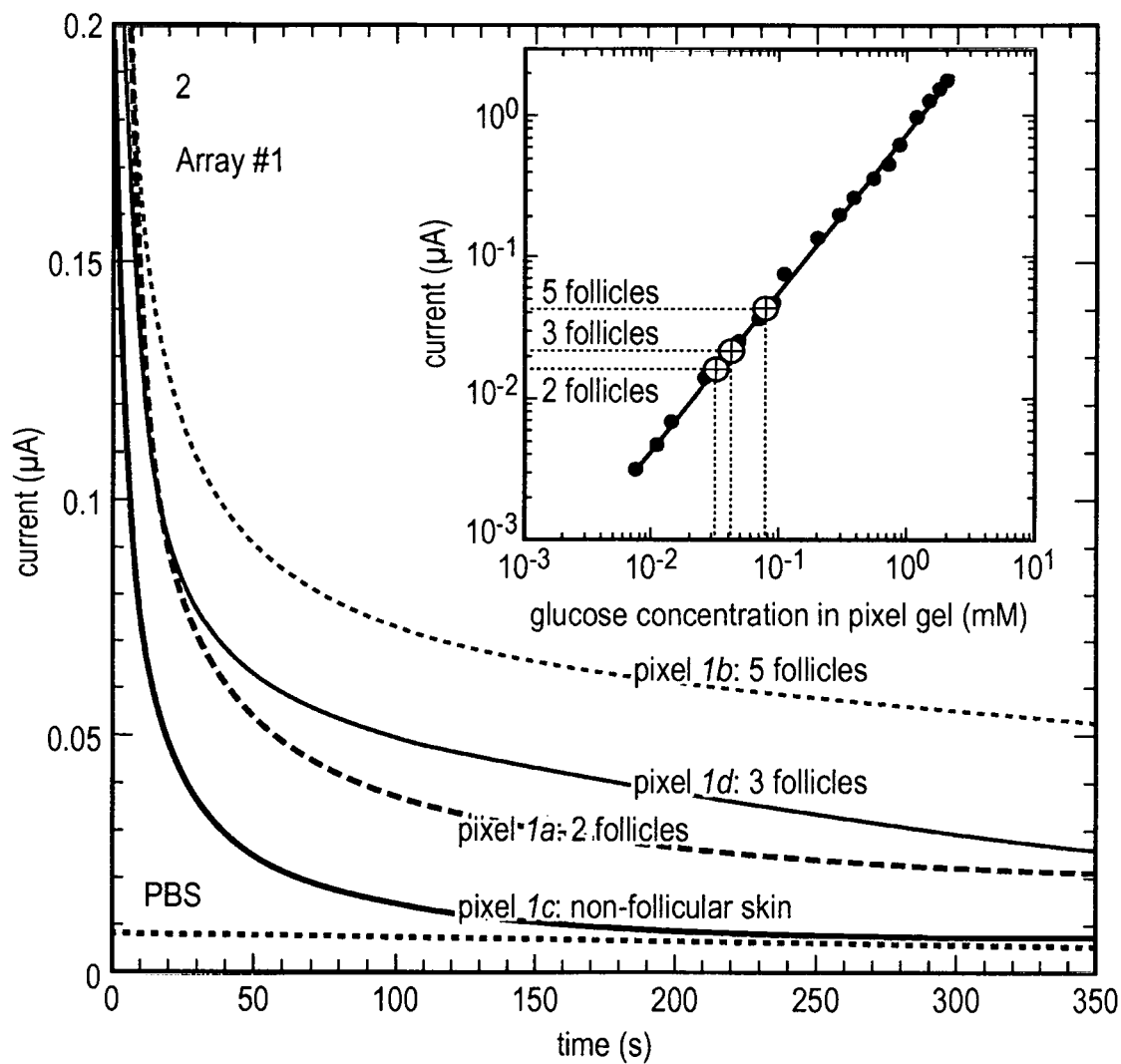
Figure 15:
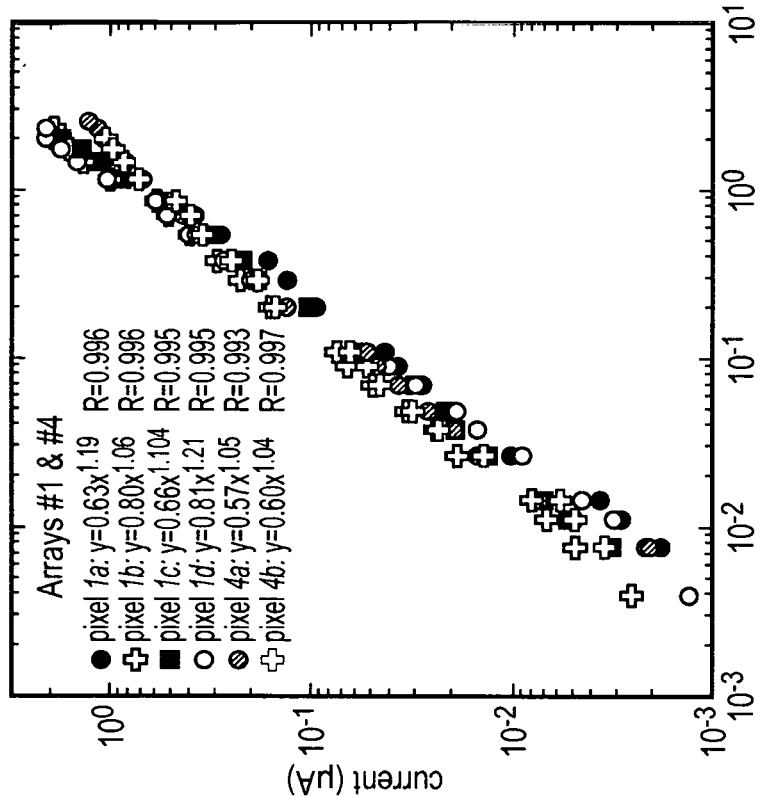
FIG. 15. Sensitivity calibration curves collected from two graphene-based arrays showing very close agreement.

FIGS. 14 and 15 contain a compilation of representative ex-vivo (porcine skin) extraction-detection experiments involving four different 2×2 graphene-based arrays realized by the strategy no. 1 described in section "Detailed discussion/Choice of materials and device realization strategies". As detailed below, the data demonstrate all the expected functional aspects: (i) targeted extraction (FIG. 14 B and C), (ii) correlation and proportionality with the number of hair follicles probed by the respective pixels (FIG. 14 B and C), (iii) capability to detect glucose extracted through a single hair follicle (FIG. 14 C), (iv) proportionality with the concentration of subdermal glucose (FIG. 14 B, panel 3), and (v) close operational characteristics of pixels within an array (FIG. 14 B, panel 1), as well as between different arrays (FIG. 15).

The functionality of such a 2×2 array has been demonstrated using parameters (extraction time and current, and subdermal glucose concentration) that are appropriate for realistic usage: e.g. 5 minutes each for extraction and detection time, 10 mM subdermal glucose concentration, 0.5 mA/cm$^2$ extraction current density, and 1 to 2 microL volume of gel within a pixel device. Dimensions of the pixels and of the various electrodes and components are compatible with those required in a final implementation (FIG. 14 A).

The array design followed the principles described in previous sections (strategy 1, see also "Choice of materials and array realization" below). For glucose extraction, the experiments used the configuration shown in FIG. 5 (c) (and labelled "configuration 3"), where reverse iontophoresis employs the largest of the Ag/AgCl electrodes (labelled with 1 on FIG. 14 A) located on two adjacent pixel devices as the anode and the cathode that form the extraction circuit. In this configuration, during half of the operation cycle, glucose is extracted in one of the pixels while, in the second half, the polarity of the extraction current is reversed, and glucose is extracted in the other pixel. In this way, the extraction and recovery of the AgCl content of each of the extraction electrodes involves sequentially two adjacent pixels. Recycling of the Ag and AgCl content within the respective electrodes is obtained by reversing the polarity of the extraction current during a period of "recovery" that follows each extraction. Electrodes labelled with 4 in FIG. 14 A play no role in this configuration. Ag/AgCl has been chosen as the material for the extraction electrode couple due to the ability of AgCl (an ionic solid) to recover its surface chemical composition after electrochemical stress, hence ensuring its stability after repeated cycles of extraction/recovery that require the electrode polarity to alternate. In contrast, the surface of pure Ag electrodes is subjected to reactions (e.g. oxidation) that can change its chemistry. It was found that after four cycles of extraction/detection performed with the array, the potential across the Ag/AgCl electrodes changed negligibly (by only ~30 mV), establishing their recovery.

FIG. 14 B, panel 2 shows the set of current-time detection curves obtained after extraction via each of the pixels of an array (for which the sensitivity calibration curves are shown in FIG. 14 B, panel 1); extraction has occurred through various number of hair follicles, as probed by the respective pixel devices. The inset of FIG. 14 B, panel 2 shows, for each of current-time detection curves, the detected current averaged along the plateau of the curve and then plotted on the sensitivity calibration curve: this allows one to determine, by interpolation, the concentration of the extracted glucose within the gel of each of the pixels. For simplicity of the analysis, the graph in the inset is the arithmetic average of the four current-concentration calibration curves shown in FIG. 14B, panel 1. In each case, the concentration of glucose thus determined is proportional to the number of follicles targeted by the respective pixel, and consistent with estimations based on the glucose follicular extraction flux determined previously. Additionally, extraction via non-follicular skin in similar conditions leads to a detected current that decays much faster than in the case of follicular extraction (FIG. 14 B, panel 2), due to the very low glucose content within the pixel gel. Altogether, these experiments unequivocally demonstrate that the array operates as designed, by exploiting the hair follicles as the preferential transdermal extraction paths for glucose. Further, FIG. 14 B, panel 3 shows the proportionality, after extraction through the same pixel device, of the detected current with the concentration of subdermal glucose. FIG. 14 C shows detection current vs time curves correlated with images of the hair follicles targeted by the respective pixels of an array, as an example of the way the extraction-detection is practically performed with the array. In this case, detection after extraction through a single follicle could also be probed.

Figure 16:
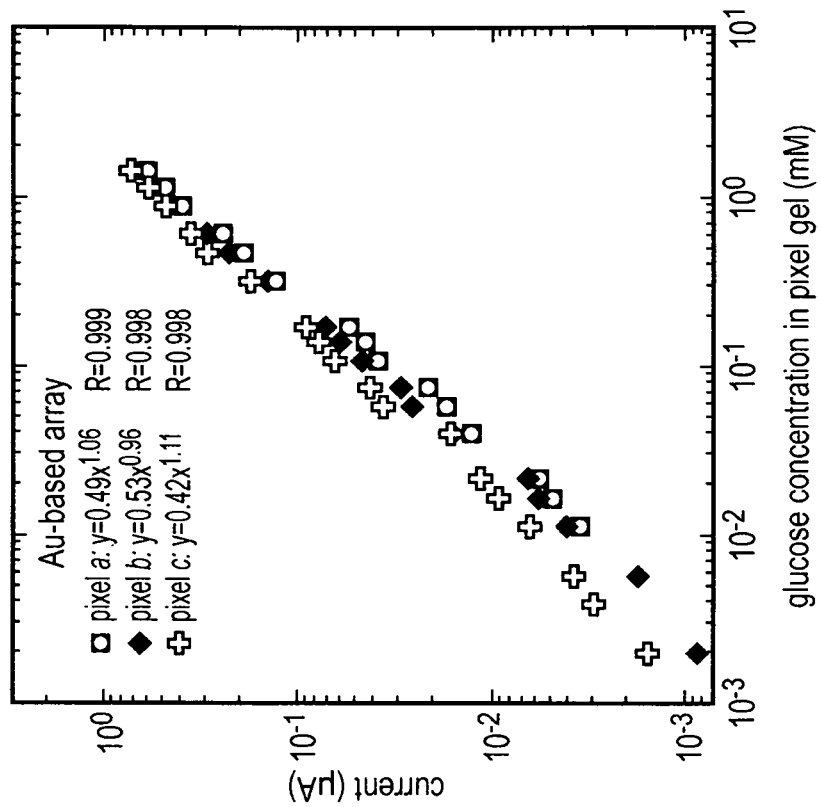
FIG. 16. Sensitivity calibration curves for an array where graphene has been replaced with an Au film. All other aspects of the array design have been left unchanged. All curves could be fitted with a slightly supralinear, single power law.

In addition to graphene (which is the material of choice to be used with the array), we also demonstrated the viability of the array design by using a more conventional sensing material, in this case gold (FIG. 16). The comparison showed that both graphene and gold, when used in conjunction with platinum nanoparticles, give very similar sensitivity calibration curves when integrated in an identical array design (compare FIG. 14 B, panel 1 with FIG. 16).

2. Choice of Materials and Array Realization

Planar Graphene-Based Array. Procedural Steps:

Graphene Wet Transfer onto a PET Sheet.

Chemical vapour deposition (CVD)-synthesized graphene, grown on a copper substrate, was transferred onto a flexible, previously polished PET sheet using a standard wet transfer procedure (Li, X., Zhu, Y., Cai, W., Borysiak, M., Han, B., Chen, D., Piner, R. D., Colombo, L. and Ruoff, R. S., *Transfer of Large-Area Graphene Films for High-Performance Transparent Conductive Electrodes*. Nano Letters, 2009, 9(12): 4359-4363). For a 2×2 array, four such graphene patches (larger than the final, desired size) were placed on the PET sheet roughly in the desired locations using a stencil mask (designed for subsequent electrode and track definition) to guide alignment. The graphene patches provide the working electrodes for each of the pixels of the array in the electrochemical detection of glucose. In order to prevent potential structural discontinuities/tearing in the graphene layer (caused either during the CVD growth or by mechanical stress during the transfer procedure) leading to electrical discontinuity of the layer, a second graphene layer is subsequently transferred on top of each of the previously transferred patches.

Electrode and Track Deposition Through Physical Vapour Deposition (Thermal Evaporation).

To deposit thin film electrodes with a defined geometry, sets of custom-made or polyimide industrial-tape (Kapton®) laser-machined stencil masks were placed successively, and aligned on top of, the PET-supported graphene patches. The stencil mask sets are tailored to the array layout, examples of such layouts being given in FIG. 4; in this specific case, the design from FIG. 4(a) has been used. A 500 nm silver film was deposited on top of a 30 nm palladium layer previously deposited to promote adhesion of the silver layer. A 500 nm thick AgCl layer was subsequently deposited on top of the silver films, to complete the reference/counter electrodes. Such thick layers of Ag and AgCl are needed to ensure a long lifetime of the reference electrode (Polk, B. J., Stelzenmuller, A., Mijares, G., MacCrehan, W. and Gaitan, M., *Ag/AgCl microelectrodes with improved stability for microfluidics*. Sensors and Actuators B: Chemical, 2006, 114(1): 239-247).

Graphene Patterning.

The graphene patches were then patterned in the predefined geometry (e.g., according to the layouts from FIG. 5). Though low energy oxygen plasma can be used to etch graphene supported by plastic substrates, in the current realization mechanical cutting (using a scalpel) was successfully employed to remove the excess graphene from the pixel patches.

Realization and Transfer of an Elastomer Membrane Designed to Support the Enzyme-Encasing Gel.

PDMS mixed with a curing agent was spin-coated on a PET support sheet and cured, leading to a 100 µm thick membrane. Circular holes (1.5-3 mm diameter) were then drilled to create sockets for the reservoir gel. After careful underwater peeling in a de-ionized water bath, the PDMS membranes were transferred onto the array with defined electrodes and tracks, ensuring alignment of the sockets to the electrochemical cell region of each pixel. The assembly was then left to dry in air.

Platinum Nanoparticle Deposition onto the Graphene Pixel Electrodes.

Platinum nanoparticles were formed and deposited on the graphene regions of the pixels through appropriate stencil masks by DC sputtering under argon. By tuning the argon gas pressure and sputtering time (of, typically, 20 s), particles of 3 to 5 nm in diameter were achieved.

Gel Casting and Enzyme Entrapping.

1 mL of a clear 2% w/v solution of agarose in PBS pH 7.4 was formed by warming above 80° C. This was then cast on a glass slide (allowing it to spread and flatten), and placed for 15 minutes in a fume hood to achieve rapid gelation. Subsequently, blocks of gel (with a volume of ca. 5 µL), with footprint areas corresponding to predetermined pixel regions, were excised. Then, 0.5 to 1 µL of enzyme solution (12 mg/mL) was placed and absorbed on the electrode side of the gel blocks. Finally, the gel blocks were placed on top of the individual pixels, inside the sockets of the PDMS membrane. In their final form, the gel blocks shrunk to about 1 to 2 µL in volume.

Planar Gold-Based Array.

All the process steps used for the graphene-based arrays remain the same, except for those involving graphene films. Instead of graphene, gold pixel regions, about 200 nm thick, were deposited by thermal evaporation in the desired locations through appropriate stencil masks.

All publications, patent and patent applications cited herein or filed with this application, including references filed as part of an Information Disclosure Statement are incorporated by reference in their entirety.

The invention claimed is:

1. A multiplexed, transdermal extraction and detection device for non-invasive monitoring of one or more substances in a subject, the device comprising an array of individually addressable sensor pixels, each sensor pixel comprising:
    (a) a substrate comprising a set of electrodes adapted to apply a current to the subject's skin for transdermally extracting one or more substances from interstitial fluid by electro-migration and/or by electro-osmosis;
    (b) a reservoir associated with the sensor pixel, the reservoir being configured to contain a volume of gel for receiving the transdermally extracted substances from the sensor pixel;
    (c) a set of detection electrodes for electrochemical detection of a concentration of the one or more transdermally extracted substances present in the reservoir associated with the sensor pixel;
    wherein the array of sensor pixels is configured so that at least one of the sensor pixels extracts the one or more substances via a preferential pathway on the subject's skin; and
    wherein the device distinguishes a sample of a transdermally extracted substance obtained via at least one preferential pathway measured at one or more sensor pixels from that extracted via other pathways measured at other sensor pixels.

2. A multiplexed, transdermal extraction and detection system for non-invasive monitoring of one or more substances in a subject, the system comprising:
    (i) a device comprising an array of individually addressable sensor pixels as defined in claim 1; and
    (ii) a data processing system that distinguishes said sample of said transdermally extracted substance obtained by the device via said preferential pathway from that extracted via other pathways, so that samples of the transdermally extracted substance via the preferential pathways are used for estimating the concentration of the one or more substances in the subject.

3. The device of claim 1, wherein the transdermally extracted substances comprise one or more markers, drugs, substances of abuse and toxins.

4. The device of claim 1, wherein the transdermally extracted substances comprise glucose.

5. The device of claim 1, wherein the substrate is flexible and transparent.

6. The device of claim 5, wherein the flexible substrate is formed from polyethylene terephthalate (PET).

7. The device of claim 1, wherein the set of electrodes comprise a silver electrode and silver/silver chloride electrode.

8. The device of claim 1, wherein the set of detection electrodes comprise a graphene electrode.

9. The device of claim 1, wherein the set of detection electrodes comprise a silver chloride electrode and a graphene electrode.

10. The device of claim 8, wherein the graphene electrode includes catalytic particles that enhance an electrochemical signal.

11. The device of claim 8, wherein the graphene electrode is made from controlled vapor deposition (CVD) graphene and a graphene-nanoflake ink.

12. The device of claim 8, wherein the graphene is patterned or printed on a substrate of the detection electrodes to provide the graphene detection electrode and electrical interconnects to other electrodes and/or external circuitry.

13. The device of claim 1, wherein the array of sensor pixels comprises at least 16 sensor pixels.

14. The device of claim 1, wherein the array of sensor pixels comprises at least 25 sensor pixels.

15. The device of claim 1, wherein the array of sensor pixels comprises between 10 and 100 sensor pixels.

16. The device of claim 1, wherein the array of sensor pixels comprises 16 or 64 sensor pixels.

17. The device of claim 1, wherein the sensor pixels have an area between 1.0 mm$^2$ and 100.0 mm$^2$.

18. The device of claim 1, wherein the sensor pixels have an area between 2.0 mm$^2$ and 50.0 mm$^2$.

19. The device of claim 1, wherein the sensor pixels have an area between 3.0 mm$^2$ and 10.0 mm$^2$.

20. The device of claim 1, wherein the volume of gel in at least one sensor pixel is less than about 30 µL.

21. The device of claim 1, wherein the volume of gel in at least one sensor pixel is between 0.2 µL and 2 µL.

22. The device of claim 1, wherein the gel in at least one sensor pixel has a thickness between 0.05 mm and 0.2 mm.

23. The device of claim 1, wherein the gel contains glucose oxidase for reacting with glucose in the sample of the transdermally extracted substance to produce hydrogen peroxide for detection by the detection electrodes.

24. The device of claim 1, wherein platinum nanoparticles are immobilized on a graphene electrode to amplify a signal from hydrogen peroxide.

25. The device of claim 1, wherein the gel is a hydrogel.

26. The device of claim 1, wherein the reservoirs of gel are encased by an elastomer to provide mechanical support for the volumes of gel within each sensor pixel array.

27. The device of claim 9, wherein graphene electrode includes catalytic particles that enhance an electrochemical signal.

28. The device of claim 10, wherein the graphene electrode is made from controlled vapor deposition (CVD) graphene and a graphene-nanoflake ink.

29. The device of claim 9, wherein graphene is patterned or printed on a substrate of the detection electrodes to provide the graphene detection electrode and electrical interconnects to other electrodes and/or external circuitry.

30. The device of claim 1, wherein the set of detection electrodes comprise a silver chloride electrode, a graphene electrode, and a platinum electrode.

31. A method for non-invasive monitoring of one or more substances in a subject, wherein the method employs a multiplexed, transdermal extraction and detection device comprising an array of individually addressable sensor pixels, each sensor pixel comprising:
(a) a substrate comprising a set of electrodes adapted to apply a current to the subject's skin for transdermally extracting one or more substances from interstitial fluid by electro-migration and/or by electro-osmosis;
(b) a reservoir associated with the sensor pixel, the reservoir being configured to contain a volume of gel for receiving the transderm ally extracted substances from the sensor pixel;
(c) a set of detection electrodes for electrochemical detection of a concentration of the one or more transdermally extracted substances present in the reservoir associated with the sensor pixel;
wherein the array of sensor pixels is configured so that at least one of the sensor pixels extracts the one or more substances via at least one preferential pathway on the subject's skin and wherein the device distinguishes a sample of a transdermally extracted substance obtained via said at least one preferential pathway measured at one or more sensor pixels from that extracted via other pathways measured at other sensor pixels;
(d) a data processing system that distinguishes said sample of said transdermally extracted substance obtained via said at least one preferential pathway from that extracted via other pathways, so that the samples of the transdermally extracted substance via the preferential pathway are used for estimating the concentration of the one or more substances in the subject's skin;
the method comprising
(i) contacting the array of sensor pixels with the skin of the subject;
(ii) using the electrodes to apply the current to the skin of the subject to transderm ally extract the one or more substances from the interstitial fluid by the electro-migration and/or by the electro-osmosis at the sensor pixels in the array;
(iii) absorbing the interstitial fluid samples into the gel reservoirs of the sensor pixels in the array;
(iv) electrochemically detecting the one or more substances absorbed into the gel reservoirs;
(v) analyzing the concentrations of the one or more substances present in the individual gel reservoirs to determine which sensor pixels extracted samples of the one or more substances via said at least one preferential pathway in the skin of the subject;
(vi) using a substance concentration from the interstitial fluid samples extracted via said at least one preferential pathway to determine the concentration of the one or more substance in the subject's skin.

\* \* \* \* \*